United States Patent
Andreano et al.

(10) Patent No.: US 10,258,604 B2
(45) Date of Patent: Apr. 16, 2019

(54) LASOFOXIFENE TREATMENT OF BREAST CANCER

(71) Applicant: Duke University, Durham, NC (US)

(72) Inventors: Kaitlyn Andreano, Durham, NC (US); Ching-yi Chang, Durham, NC (US); Donald P. McDonnell, Chapel Hill, NC (US); Stephanie L. Gaillard, Durham, NC (US)

(73) Assignee: Duke University, Durham, NC (US)

( * ) Notice: Subject to any disclaimer, the term of this patent is extended or adjusted under 35 U.S.C. 154(b) by 0 days.

(21) Appl. No.: 15/939,218

(22) Filed: Mar. 28, 2018

(65) Prior Publication Data

US 2018/0221335 A1 Aug. 9, 2018

Related U.S. Application Data

(63) Continuation of application No. 15/729,320, filed on Oct. 10, 2017, now abandoned.

(60) Provisional application No. 62/502,299, filed on May 5, 2017, provisional application No. 62/457,759, filed on Feb. 10, 2017, provisional application No. 62/406,859, filed on Oct. 11, 2016.

(51) Int. Cl.
| | |
|---|---|
| *A61K 31/40* | (2006.01) |
| *A61K 31/00* | (2006.01) |
| *A61P 5/00* | (2006.01) |
| *A61P 35/04* | (2006.01) |
| *A61K 9/00* | (2006.01) |
| *A61K 45/06* | (2006.01) |
| *C12Q 1/6886* | (2018.01) |
| *A61P 35/00* | (2006.01) |

(52) U.S. Cl.
CPC ............ *A61K 31/40* (2013.01); *A61K 9/0053* (2013.01); *A61K 31/00* (2013.01); *A61K 45/06* (2013.01); *A61P 5/00* (2018.01); *A61P 35/00* (2018.01); *A61P 35/04* (2018.01); *C12Q 1/6886* (2013.01); *C12Q 2600/112* (2013.01); *C12Q 2600/156* (2013.01)

(58) Field of Classification Search
CPC .............................. A61K 31/00; A61K 31/40
See application file for complete search history.

(56) References Cited

U.S. PATENT DOCUMENTS

| | | | |
|---|---|---|---|
| 5,552,412 A | 9/1996 | Cameron et al. |
| 5,948,809 A | 9/1999 | Chiu et al. |
| 6,060,503 A | 5/2000 | Labrie et al. |
| 6,107,331 A | 8/2000 | MacLean et al. |
| 6,153,622 A | 11/2000 | Cameron et al. |
| 6,204,286 B1 | 3/2001 | Cameron et al. |
| 6,232,476 B1 | 5/2001 | Chiu |
| 6,274,618 B1 | 8/2001 | MacLean et al. |
| 6,323,232 B1 | 11/2001 | Ke et al. |
| 6,323,345 B1 | 11/2001 | Chiu |
| 6,355,670 B1 | 3/2002 | MacLean et al. |
| 6,395,911 B1 | 5/2002 | Chiu |
| 6,403,611 B2 | 6/2002 | MacLean et al. |
| 6,436,977 B1 | 8/2002 | Thompson |
| 6,441,193 B1 | 8/2002 | Cameron et al. |
| 6,511,986 B2 | 1/2003 | Zhang et al. |
| 6,512,002 B2 | 1/2003 | Lee et al. |
| 6,613,796 B2 | 9/2003 | MacLean et al. |
| 6,906,202 B2 | 6/2005 | McLaughlin et al. |
| 6,911,456 B2 | 6/2005 | MacLean et al. |
| RE39,558 E | 4/2007 | Cameron et al. |
| 7,255,984 B2 | 8/2007 | Ke et al. |
| 7,358,374 B2 | 4/2008 | McLaughlin et al. |
| 7,553,500 B2 | 6/2009 | Gierer |
| 9,018,244 B2 | 4/2015 | Kushner et al. |
| 9,204,286 B1 | 12/2015 | Annan et al. |
| 2001/0025051 A1 | 9/2001 | Cameron et al. |
| 2002/0132816 A1 | 9/2002 | Cameron et al. |
| 2003/0040510 A1 | 2/2003 | Labrie |
| 2003/0114440 A1 | 6/2003 | Lee et al. |
| 2004/0009994 A1 | 1/2004 | MacLean et al. |
| 2004/0053898 A1 | 3/2004 | Fritzemeier et al. |
| 2004/0057992 A1 | 3/2004 | Gierer |
| 2004/0110689 A1 | 6/2004 | Garnick |
| 2005/0148625 A1 | 7/2005 | MacLean et al. |
| 2009/0012052 A1 | 1/2009 | Coopersmith et al. |
| 2010/0317712 A1 | 12/2010 | Cameron et al. |
| 2011/0015134 A1 | 1/2011 | Retsky |
| 2011/0182888 A1 | 7/2011 | Ordentlich et al. |
| 2012/0052508 A1 | 3/2012 | Bilal et al. |
| 2014/0079665 A1 | 3/2014 | Goetsch et al. |
| 2014/0221329 A1 | 8/2014 | Cronin et al. |

(Continued)

FOREIGN PATENT DOCUMENTS

| | | |
|---|---|---|
| WO | WO 96/21656 A1 | 7/1996 |
| WO | WO 97/16434 A1 | 5/1997 |
| WO | WO 97/31640 A1 | 9/1997 |

OTHER PUBLICATIONS

PCT Invitation to Pay Additional Fees, PCT Application No. PCT/US17/55974, Dec. 1, 2017, 3 pages.
"Adjuvant Bisphosphonate Treatment in Early Breast Cancer: Meta-Analyses of Individual Patient Data from Randomised Trials," Lancet, 2015, [Contributors: R. Coleman et l.], pp. 1353-1361, vol. 386.
Angus, L., "ESR1 Mutations: Moving Towards Guiding Treatment Decision-Making in Metastatic Breast Cancer Patients," Cancer Treatment Reviews, 2017, pp. 33-40, vol. 52.

(Continued)

*Primary Examiner* — Samira J Jean-Louis
(74) *Attorney, Agent, or Firm* — Fenwick & West LLP

(57) ABSTRACT

The disclosure provides methods for treating estrogen receptor positive (ER+) cancer in women with an effective amount of lasofoxifene, a pharmaceutically acceptable salt thereof, or a prodrug thereof. The disclosure also includes the detection of the Estrogen Receptor 1 (ESR1) gene mutations that lead to endocrine resistance and treatment of endocrine resistant ER+ cancers.

17 Claims, 3 Drawing Sheets

Specification includes a Sequence Listing.

(56) References Cited

U.S. PATENT DOCUMENTS

| | | |
|---|---|---|
| 2015/0258099 A1 | 9/2015 | Hager et al. |
| 2015/0274640 A1 | 10/2015 | Wardell et al. |
| 2016/0201135 A1 | 7/2016 | Cronin et al. |
| 2016/0324808 A1 | 11/2016 | Wardell et al. |
| 2017/0027928 A1 | 2/2017 | McDonnell et al. |
| 2017/0202823 A1 | 7/2017 | Wardell et al. |
| 2017/0202854 A1 | 7/2017 | Genkin et al. |
| 2018/0098963 A1 | 4/2018 | Andreano et al. |

OTHER PUBLICATIONS

"Assessment Report for Fablyn, International Nonproprietary Name: lasofoxifene," European Medicines Agency, 2009, 44 pages.

Bardia, A. et al., "Metastatic Breast Cancer with ESR1 Mutation: Clinical Management Considerations From the Molecular and Precision Medicine (MAP) Tumor Board at Massachusetts General Hospital," The Oncologist, 2016, pp. 1035-1040, vol. 21.

Chang, K.C.N. et al., "Gene Expression Profiling Studies of Three SERMs and Their Conjugated Estrogen Combinations in Human Breast Cancer Cells: Insights Into the Unique Antagonistic Effects of Bazedoxifene on Conjugated Estrogens," Journal of Steroid Biochemistry and Molecular Biology, 2010, pp. 117-124, vol. 118.

Cohen, L.A. et al., "LAS: A Novel Selective Estrogen Receptor Modulator with Chemopreventive and Therapeutic Activity in the N-Nitroso-N-Methylurea-Induced Rat Mammary Tumor Model," Cancer Research, Dec. 15, 2001, pp. 8683-8688, vol. 61.

Cummings, S.R. et al., "Lasofoxifene in Postmenopausal Women with Osteoporosis," The New England Journal of Medicine, Feb. 25, 2010, pp. 686-696, vol. 362, No. 8. [With Supplement].

Cuzick, J. et al., "Selective Oestrogen Receptor Modulators in Prevention of Breast Cancer: An Updated Meta-Analysis of Individual Participant Data," The Lancet, May 25, 2013, pp. 1827-1834, vol. 381.

Dukelow, T. et al., "CDK4/6 Inhibitors in Breast Cancer," Anti-Cancer Drugs, 2015, pp. 788-806, vol. 26, No. 8.

Fanning, S.W. et al., "Estrogen Receptor Alpha Somatic Mutations Y537S and D538G Confer Breast Cancer Endocrine Resistance by Stabilizing the Activating Function-2 Binding Conformation," eLife, 2016, pp. 1-25, vol. 5, e12792.

Gardner, M. et al., "Clinical Pharmacology of Multiple Doses of Lasofoxifene in Postmenopausal Women," J Clin Pharmacol, 2006, pp. 52-58, vol. 46, No. 1.

Goldstein, S.R. et al., "Postmenopausal Evaluation and Risk Reduction with Lasofoxifene (PEARL) Trial: 5-Year Gynecological Outcomes," Menopause: The Journal of The North American Menopause Society, 2011, pp. 17-22, vol. 18, No. 1.

Goss, P.E. et al., "Extending Aromatase-Inhibitor Adjuvant Therapy to 10 Years," The New England Journal of Medicine, Jun. 5, 2016, pp. 1-11.

Jeselsohn, R. et al., "Emergence of Constitutively Active Estrogen Receptor-α Mutations in Pretreated Advanced Estrogen Receptor-Positive Breast Cancer," Clinical Cancer Research, Apr. 1, 2014, pp. 1757-1767, vol. 20, No. 7.

Jeselsohn, R. et al., "ESR1 Mutations—A Mechanism for Acquired Endocrine Resistance in Breast Cancer," Clinical Oncology, Oct. 2015, pp. 573-583, vol. 12.

Johnston, S.R.D., "Endocrine Manipulation in Advanced Breast Cancer: Recent Advances with SERM Therapies," Clinical Cancer Research, Dec. 2001 (Suppl), pp. 4376s-4387s, vol. 7.

Johnston, S.R.D., "Optimising the Treatment of ER+ Metastatic Breast Cancer," UK Breast Cancer Meeting, Nov. 21, 2014, 45 pages.

Johnston, S.R.D., "New Strategies in Estrogen Receptor-Positive Breast Cancer," Clinical Cancer Research, 2010, pp. 1979-1987, vol. 16.

Joseph, J.D. et al., "The Selective Estrogen Receptor Downregulator GDC-0810 is Efficacious in Diverse Models of ER+ Breast Cancer," eLife, 2016, pp. 1-34, vol. 5, e15828.

Lacroix, A.Z. et al., "Breast Cancer Incidence in the Randomized PEARL Trial of Lasofoxifene in Postmenopausal Osteoporotic Women," J Natl Cancer Intstl, Nov. 17, 2000, pp. 1706-1715, vol. 102, Issue 22.

Lipton, A. et al., "Effect of Denosumab Versus Zoledronic Acid in Preventing Skeletal-Related Events in Patients with Bone Metastases by Baseline Characteristics," European Journal of Cancer, 2016, pp. 75-83, vol. 53.

Maximov, P.Y. et al., The Discovery and Development of Selective Estrogen Receptor Modulators (SERMs) for Clinical Practie, Current Clinical Pharmacology, 2013, pp. 135-155, vol. 8, No. 2.

Mcdonnell, D.P. et al., "Oral Selective Estrogen Receptor Downregulators (SERDs), a Breakthrough Endocrine Therapy for Breast Cancer," Journal of Medicinal Chemistry, 2015, pp. 4883-4887, vol. 58, No. 12.

Merenbakh-Lamin, K. et al., "D538G Mutation in Estrogen Receptor-α: A Novel Mechanism for Acquired Endocrine Resistance in Breast Cancer," Cancer Research, Dec. 1, 2013, pp. 6856-6864, vol. 73, No. 23.

Mocellin, S. et al., "Breast Cancer Chemoprevention: A Network Meta-Analysis of Randomized Controlled Trials," JNCI J Natl. Cancer Inst., 2016, 9 pages, vol. 108, No. 2.

Nagel, S.C. et al., "Development of an ER Action Indicator Mouse for the Study of Estrogens, Selective ER Modulators (SERMs), and Xenobiotics," Endocrinology, 2001, pp. 4721-4728, vol. 142, No. 11.

Niu, J. et al., "Incidence and Clinical Significance of ESRI Mutations in Heavily Pretreated Metastatic Breast Cancer Patients," OncoTargets and Therapy, Nov. 11, 2015, pp. 3323-3328, vol. 8.

Norris, J. et al., "Identification of a New Subclass of Alu DNA Repeats Which Can Function as Estrogen Receptor-dependent Transcriptional Enhancers," The Journal of Biological Chemistry, Sep. 29, 1995, pp. 22777-22782, vol. 270, No. 39.

Ottanelli, S., "Prevention and Treatment of Bone Fragility in Cancer Patient," Clinical Cases in Mineral and Bone Metabolism, 2015, pp. 116-129, vol. 12, No. 2.

Radhi, S., "Molecular Changes During Breast Cancer and Mechanisms of Endocrine Therapy Resistance," Progress in Molecular Biology and Translational Science, Chapter Twelve, 2016, pp. 539-562, vol. 144.

Robinson, D.R. et al., "Activating ESR1 Mutations in Hormone-Resistant Metastatic Breast Cancer," Nature Genetics, Dec. 2013, pp. 1446-1451, vol. 45, No. 12.

Santen, R.J. et al., "Modeling of the Growth Kinetics of Occult Breast Tumors: Role in Interpretation of Studies of Prevention and Menopausal Hormone Therapyy," Cancer Epidemiology, Biomarkers & Prevention, 2012, pp. 1038-1048, vol. 21.

Sefrioui, D. et al., "Short Report: Monitoring ESR1 Mutations by Circulating Tumor DNA in Aromatase Inhibitor Resistant Metastatic Breast Cancer," International Journal of Cancer, 2015, pp. 2513-2519, vol. 137.

Song, Y. et al., "Effects of the Conjugated Equine Estrogen/ Bazedoxifene Tissue-Selective Estrogen Complex (TSEC) on Mammary Gland and Breast Cancer in Mice," Endocrinology, Dec. 1, 2012, pp. 5706-5715, vol. 153, No. 12.

Srinivasan, S. et al., "Full Antagonism of the Estrogen Receptor Without a Prototypical Ligand Side Chain," Nature Chemical Biology, Jan. 2017, pp. 1-12, vol. 13.

Stearns, V. et al., "Gene Mutation Profiling of Breast Cancers for Clinical Decision Making," JAMA Oncology, Aug. 2015, pp. 569-570, vol. 1, No. 5.

Thomas, C. et al., "Estrogen Receptor Mutations and Functional Consequences for Breast Cancer," Trends Endocrinal Metab., Sep. 2015, pp. 467-476, vol. 26, No. 9.

Toy, W. et al., "ESR1 Ligand Binding Domain Mutations in Hormone-Resistant Breast Cancer," Nat Genet., Dec. 2013, pp. 1439-1445, vol. 45, No. 12.

Vajdos, F.F. et al., "The 2.0 Å Crystal Structure of the ERα Ligand-Binding Domain Complexed with Lasofoxifene," Protein Science, 2007, pp. 897-905, vol. 16.

Wang, X-N. et al., "Lasofoxifene Enhances Vaginal Mucus Formation Without Causing Hypertrophy and Increases Estrogen Receptor

(56) References Cited

OTHER PUBLICATIONS

β and Androgen Receptor in Rats," Menopause: The Journal of The North American Menopause Society, 2006, pp. 609-620, vol. 13, No. 4.
Wardell, S.E. et al., "Bazedoxifene Exhibits Antiestrogenic Activity in Animal Models of Tamoxifen-Resistant Breast Cancer: Implications for Treatment of Advanced Disease," Clinical Cancer Research, 2013, pp. 2420-2431, vol. 19.
Wardell, S.E. et al., "Efficacy of SERD/SERM Hybrid-CDK4/6 Inhibitor Combinations in Models of Endocrine Therapy-Resistant Breast Cancer," Clinical Cancer Research, Nov. 15, 2015, pp. 5121-5130, vol. 21, No. 22.
PCT International Search Report and Written Opinion, PCT Application No. PCT/US17/55974, Jan. 29, 2018, 20 pages.
Berrodin, T.J. et al., "Differential Biochemical and Cellular Actions of Premarin Estrogens: Distinct Pharmacology of Bazedoxifene-Conjugated Estrogens Combination," Mol Endocrinol., Jan. 1, 2009, pp. 74-85, vol. 23, No. 1.
Bouchardy, C, et al. "Lung Cancer Mortality Risk Among Breast Cancer Patients Treated with Anti-Estrogens," Cancer, Mar. 15, 2011, pp. 1288-1295.
Fribbens, C. et al., "Plasma ESR1 Mutations and the Treatment of Estrogen Receptor-Positive Advanced Breast Cancer," Journal of Clinical Oncology, Sep. 1, 2016, pp. 2961-2968, vol. 34, No. 25.
Gelsomino, L. et al., "ESR Mutations Affect Anti-Proliferative Responses to Tamoxifen Through Enhanced Cross-Talk with IGF Signaling," Breast Cancer Res. Treat., Jun. 2016, pp. 253-265, vol. 157, No. 2.
Jeselsohn, R. et al., "ESR1 Mutations—A Mechanism for Acquired Endocrine Resistance in Breast Cancer," Nature Reviews Clinical Oncology, Oct. 2015, pp. 573-583, vol. 12.
Jeselsohn, R. et al., Emergence of Constitutively Active Estrogen-Receptor-α Mutations in Pretreated Advanced Estrogen Receptor-Positive Breast Cancer, Human Cancer Biology, Clin. Cancer Res., 2014, pp. 1757-1767, vol. 20, No. 7.
Johnston, S., "Endocrine Manipulation in Advanced Breast Cancer: Recent Advances with SERM Therapies," Clinical Cancer Research, Dec. 2001, pp. 4376s-4387s, vol. 7.
Johnston, S.R. et al., "Fulvestrant Plus Anastrozole or Placebo Versus Exemestane Alone After Progression on Non-Steroidal Aromatase Inhibitors in Postmenapausal Patients with Hormone-Receptor-Positive Locally Advanced or Metastatic Breast Cancer (SoFEA): A Composite, Multicentre, Phase 3 Ransomised Trial," The Lancet Oncology Sep. 2013, pp. 989-998, vol. 14, No. 10.
Ke, H.Z. et al., Effects of CP-336,156, a New, Nonsteroidal Estrogen Agonist/Antagonist, on Bone, Serum Cholesterol, Uterus, and Body Composition in Rat Models, Endocrinology, 1998, pp. 2068-2076, vol. 139, No. 4.
Ke, H.Z. et al., "Long-Term Treatment of Lasofoxifene Preserves Bone Mass and Bone Strength and Does Not Adversely Affect the Uterus in Ovariectomized Rats," Endocrinology, 2004, pp. 1996-2005, vol. 145, No. 4.
Komm, B.S. et al., "Developing a SERM: Stringent Preclinical Selection Criteria Leading to an Acceptable Candidate (WAY-140424) for Clinical Evaluation," Ann N Y Acad Sci., 2001, pp. 317-326. vol. 949.
Lacroix, A et al., "Breast Cancer Incidence in the Randomized PEARL Trial of Lasofoxifene in Postmenopausal Osteoporotic Women," J Natl Cancer Inst., Nov. 17, 2010, pp. 1706-1715, vol. 102, Issue 22.
Lother, S.A. et al., "Antiestrogen Use and Survival of Women with Non-Small Cell Lung Cancer in Manitoba, Canada," Horm Cancer, 2013, pp. 270-276, vol. 4.
Maurer, C. et al., "New Agent for Endocrine Resistance in Breast Cancer", The Breast, 2017, 12, pp. 1-11, vol. 34.
Mcdonnell, D.P. et al., "The Molecular Mechanisms Underlying the Pharmacological Actions of ER Modulators: Implications for New Drug Discovery in Breast Cancer," Current Opinion in Pharmacology, Dec. 2010, pp. 620-628, vol. 10, No. 6.

Miller, W.R. et al., "Understanding the Mechanisms of Aromatase Inhibitor Resistance," Breast Cancer Research, 2012, pp. 1-11, vol. 14: 201.
Parise, C.A. et al., "Breast Cancer Survival Defined by the ER/PR/HER2 Subtypes and a Surrogate Classification According to Tumor Grade and Immunohistochemical Biomarkers," Journal of Cancer Epidemiology, 2014, Article ID 469251, pp. 1-11.
PCT Invitation to Pay Additional Fees, PCT Application No. PCT/US2017/055970, Jan. 18, 2018, 16 pages.
PCT International Search Report and Written Opinion, PCT Application No. PCT/US2017/055970, dated Mar. 14, 2018, 24 pages.
Robinson, D.R. et al., "Activating ESR1 Mutations in Hormone-Resistant Metastatic Breast Cancer," Nature Genetics, Dec. 2013, pp. 1446-1453, vol. 45, No. 12.
Robertson, J.F.R. et al., "Fulvestrant 500 mg Versus Anastrozole 1 mg for Hormone Receptor-Positive Advanced Breast Cancer (Falcon): An International, Randomised, Double-Blind, Phase 3 Trial," The Lancet, Dec. 2016, pp. 2997-3005, vol. 388, No. 10063.
Sflomos, G. et al., "A Preclinical Model for ERα-Positive Breast Cancer Points to the Epithelial Microenvironment as Determinant of Luminal Phenotype and Hormone Response," Cancer Cell, 2016 pp. 407-422, vol. 29.
Shelly, W. et al., "Selective Estrogen Receptor Modulators: An Update on Recent Clinical Findings," Obstetrical and Gynecological Survey, Feb. 29, 2008, pp. 163-181, vol. 63, No. 3.
Shi, Y. et al., A Genome-Wide Association Study Identifies Two New Cervical Cancer Susceptibility Loci at 4q12 and 17q12, Nature Genetics, Aug. 2013, pp. 918-924, vol. 45, No. 8.
Spoerke, J.M. et al., "Heterogeneity and Clinical Significance of ESR1 Mutations in ER-Positive Metastatic Breast Cancer Patients Receiving Fulvestrant," Nature Communications, May 2016, pp. 1-10, vol. 13, No. 7.
Toy, W. et al., "Activating ESR1 Mutations Differentially Affect the Efficacy of ER Antagonists," Cancer Discovery, Mar. 2017, pp. 277-287, vol. 7.
Turner, N. et al., "Genetic Hegerogeneity and Cancer Drug Resistance," Lancet Oncology, Apr. 2012, pp. e178-85, vol. 13.
Wardell, S.E. et al., "The Turnover of Estrogen Receptor α by the Selective Estrogen Receptor Degrader (SERD) Fulvestrant is a Saturable Process That is not Required for Antagonist Efficacy," Biochem Pharmacol., Jul. 15, 2011, pp. 122-130, vol. 82, No. 2.
U.S. Appl. No. 08/803,733, filed Feb. 21, 1997, Inventors: David B. Maclean et al.
U.S. Appl. No. 09/575,310, filed May 19, 2000, Inventor Charles K.F. Chiu.
U.S. Appl. No. 09/757,423, filed Jan. 10, 2001, Inventor Andrew G. Lee et al.
U.S. Appl. No. 09/656,273, filed Sep. 6, 2000, Inventor David D. Thompson.
U.S. Appl. No. 10/397,654, filed Mar. 26, 2003, Inventors Robert W. McLaughlin.
U.S. Appl. No. 10/612,679, filed Jul. 1, 2003, Inventor Daniel S. Gierer.
Bahreini, A. et al., "Mutation Site and Context Dependent Effects of ESR1 Mutation in Genome-Edited Breast Cancer Cell Models," Breast Cancer Research, 2017, 19:60.
Baselga, J. et al., "Everolimus in Postmenopausal Hormone-Receptor-Positive Advanced Breast Cancer," NEJM, 2012, 366:520-529.
Connor, C. E. et al., "Circumventing Tamoxifen Resistance in Breast Cancers Using Antiestrogens That Induce Unique Conformational Changes in the Estrogen Receptor," Cancer Res., 2001, 61:2917-2922.
C4 Dayan, G. et al., "Tamoxifen and Raloxifene Differ in Their Functional Interactions with Aspartate 351 of Estrogen Receptor," Molecular Pharmacology, 2006, 70:579-588.
Dusell, C. D. et al., "Regulation of Aryl Hydrocarbon Receptor Function by Selective Estrogen Receptor Modulators," Mol Endocrinol., 2010, 24:33-46.
Jeselsohn, R. et al., "Allele-Specific Chromatin Recruitment and Therapeutic Vulnerabilities of ESR1 Activating Mutations," Cancer Cell, 2018, 33:173-186.
Lai, A. et al., "Identification of GDC-0810 (ARN-810), an Orally Bioavailable Selective Estrogen Receptor Degrader (SERD) that

(56) References Cited

OTHER PUBLICATIONS

Demonstrates Robust Activity in Tamoxifen-Resistant Breast Cancer Xenografts," J Med Chem., 2015, 58:4888-4904.

Levenson, A. S. et al., "The Key to the Antiestrogenic Mechanism of Raloxifene is Amino Acid 351 (Aspartate) in the Estrogen Receptor," Cancer Res., 1998, 58:1872-1875.

Liu, H. et al., "Structure-Function Relationships of the Raloxifene-Estrogen-Raloxifene-Estrogen Receptor-Alpha Complex for Regulating Transforming Growth Factor-Alpha Expression in Breast Cancer Cells," J Biol Chem., 2002, 277:9189-9198.

Ma, C.K. et al., "Mechanisms of Aromatase Inhibitor Resistance," Nat. Rev. Cancer, 2015, 15:261-275.

Martin, L.-A. et al., "Discovery of Naturally Occurring ESR1 Mutations in Breast Cancer Cell Lines Modelling Endocrine Resistance," Nat Commun., 2017, 8:1865.

Mcdonnell, D. P. et al., "Analysis of Estrogen Receptor Function in Vitro Reveals Three Distinct Classes of Antiestrogens," Mol Endocrinol. 1995, 9:659-69.

Mcdonnell, D. P. et al., "Identification of a Negative Regulatory Function for Steroid Receptors." Proc Natl Acad Sci U S A, 1992, 89:10563-10567.

Mcdonnell, D.P. et al., "Neomorphic ERα Mutations Drive Progression in Breast Cancer and Present a Challenge for New Drug Discovery," Cancer Cell, 2018, 33:153-155.

Paige, L. A. et al., "Estrogen Receptor(ER) Modulators Each Induce Distinct Conformational Changes in ERa and ERb," Proc. Natl. Acad. Sci. USA, 1999, 96:3999-4004.

Patel, H. K. et al., "Selective Estrogen Receptor Modulators (SERMs) and Selective Estrogen Receptor Degraders (SERDs) in Cancer Treatment," Pharmacol Ther., 2018, 186:1-24.

Razavi et al., "The Genomic Landscape of Endocrine-Resistant Advanced Breast Cancers," Cancer Cell, 2018, 34:427-438.

Robinson, D.R. et al., "Activating ESR1 Mutations in Hormone-Resistant Metastatic Breast Cancer," Nature Genetics, 2013, 45:1446-1451.

Santen, R. J et al., "Modeling of the Growth Kinetics of Occult Breast tumors: Role in Interpretation of Studies of Prevention and Menopausal Hormone Therapy," Cancer Epidemiol Biomarkers Prev, 2012, 21:1038-1048.

Schiavon, G. et al., "Analysis of ESR1 Mutation in Circulating Tumor DNA Demonstrates Evolution During Therapy for Metastatic Breast Cancer," Clin. Cancer Res., 2013, 20:1757-1767.

Traboulsi, T. et al., "Antiestrogens: Structure Activity Relationships and Use in Breast Cancer Treatment," Journal of Molecular Endocrinology, 2017, 58:R15-R31.

Tzukerman, M. T. et al., "Human Estrogen Receptor Transactivational Capacity is Determined by Both Cellular and Promoter Context and Mediated by Two Functionally Distinct Intramolecular Regions," Mol Endocrinol., 1994, 8:21-30.

Wang, P. et al., "Sensitive Detection of Mono- and Polyclonal esr1 Mutations in Primary Tumors, Metastatic Lesions, and Cell-Free DNA of Breast Cancer Patients," Clin Cancer Res., 2016, 22:1130-1137.

Wijayaratne, A. L. et al., "Comparative Analyses of the Mechanistic Differences Among Antiestrogens," Endocrinology, 1999, 140: 5828-5840.

LASOFOXIFENE TREATMENT OF BREAST CANCER

1. CROSS-REFERENCE TO RELATED APPLICATIONS

This application is a continuation of co-pending U.S. application Ser. No. 15/729,320, filed Oct. 10, 2017, which claims the benefit of U.S. Provisional Application Nos. 62/502,299, filed May 5, 2017; 62/457,759, filed Feb. 10, 2017; and 62/406,859, filed Oct. 11, 2016, each of which is incorporated in its entirety by reference.

2. SEQUENCE LISTING

The instant application contains a Sequence Listing which has been submitted via EFS-Web and is hereby incorporated by reference in its entirety. Said ASCII copy, created on Mar. 28, 2017, is named 40238US_CRF_sequencelisting.txt, and is 2,195 bytes in size.

3. BACKGROUND OF THE INVENTION

Estrogen receptor positive (ER$^+$) breast cancers are a group of breast cancers that express estrogen receptor α (ERα). Approximately 70% of breast cancers are ER$^+$ and are, therefore, treated with endocrine therapy. Endocrine therapy has led to significant improvement in outcome of women with ER$^+$ breast cancer by lowering the level of estrogen or blocking estrogen signaling. However, its effectiveness is limited by intrinsic and acquired endocrine resistance.

Recent studies have shown evidence for the temporal selection of functional Estrogen Receptor 1 (ESR1) gene mutations as potential drivers of endocrine resistance during the progression of ER$^+$ breast cancer. See Jeselsohn et al., *Clinical Cancer Research* 20(7): 1757-1767 (2014). The mutations in ESR1, the gene encoding ERα, change the conformation of the ERα protein, increase its interaction with its co-activators, promote an active form of the receptor in absence of hormone, and assist tumor cells in evading hormonal treatment. See Thomas and Gustafsson, *Trends in Endocrinology and Metabolism* 26(9): 467-476 (2015).

There thus remains a need to develop new therapeutic strategies that are effective to treat tumors harboring mutations in ESR1, and that can therefore be used to treat breast cancer patients who have developed endocrine resistance or who are at risk of developing endocrine resistance.

4. SUMMARY OF THE INVENTION

We engineered ERα expression constructs to express four ESR1 mutations in the ligand binding domain (LBD) of the ERα protein, Y537S, Y537N, Y537C, and D538G, and introduced these expression constructs into cells in culture. These mutations are found in ER$^+$ metastatic breast cancer patients who have been treated with endocrine therapy. See Jeselsohn et al., *Nature Reviews Clinical Oncology* 12(10): 573-583 (2015); Jeselsohn et al., *Clinical Cancer Research* 20(7): 1757-1767 (2014); Robinson et al., *Nature Genetics* 45(12): 1446-1451 (2013); Thomas and Gustafsson, *Trends in Endocrinology and Metabolism* 26(9): 467-476 (2015); and Toy et al., *Nature Genetics* 45(12): 1439-1445 (2013).

Using an estrogen receptor-responsive reporter construct, we confirmed in an ovarian cell line and in a breast cancer cell line that all mutants are constitutively active as compared to wild type ERα. We then treated the cells with lasofoxifene, a selective ER modulator (SERM), and found that lasofoxifene effectively inhibited the transcriptional activity of the ERα LBD mutants in a dose-response manner, at concentrations that are clinically achievable.

In a second series of experiments, we confirmed that lasofoxifene is able to reduce viability of the breast cancer cell line MCF7 stably transfected with either the Y537S or D538G ESR1 mutant receptor, at clinically achievable concentrations.

Accordingly, in a first aspect, a method of treating locally advanced or metastatic breast cancer in women is presented. The method comprises selecting for treatment a patient who has been diagnosed with estrogen receptor positive (ER$^+$) locally advanced or metastatic breast cancer, and administering to the selected patient an effective amount of lasofoxifene, a pharmaceutically acceptable salt thereof, or a prodrug thereof.

In various embodiments, the selected patient has previously been treated with one or more lines of endocrine therapy. In certain embodiments, the patient has previously been treated with a plurality of lines of endocrine therapy.

In some embodiments, the endocrine therapy that the patient has previously been treated with is a selective ER modulator (SERM). In certain embodiments, the SERM is tamoxifen, raloxifene, bazedoxifene, toremifene, or ospemifene.

In some embodiments, the endocrine therapy that the patient has previously been treated with is a selective ER degrader (SERD). In certain embodiments, the SERD is fulvestrant, RAD1901, ARN-810 (GDC-0810), or AZD9496.

In some embodiments, the endocrine therapy that the patient has previously been treated with is an aromatase inhibitor. In certain embodiments, the aromatase inhibitor is exemestane (Aromasin®), letrozole (Femara®), or anastrozole (Arimidex®).

In some embodiments, the patient has disease progression after endocrine therapy. In some embodiments, the patient is resistant to endocrine therapy.

In various embodiments, the patient's cancer has at least one gain of function missense mutation within the ligand binding domain (LBD) of the Estrogen Receptor 1 (ESR1) gene. In some embodiments, the patient has previously been determined to have at least one gain of function missense mutation within the ligand binding domain (LBD) of the Estrogen Receptor 1 (ESR1) gene. In certain embodiments, the method further comprises the earlier step of: determining that the patient has at least one gain of function missense mutation within the ligand binding domain (LBD) of the Estrogen Receptor 1 (ESR1) gene.

In some embodiments, the at least one of gain of function missense mutation is in any one of amino acids D538, Y537, L536, P535, V534, S463, V392, or E380.

In certain embodiments, the at least one gain of function missense mutation is in the amino acid D538. In some preferred embodiments the mutation is D538G.

In certain embodiments, the at least one gain of function missense mutation is in the amino acid Y537. In some embodiments, the mutation is Y537S, Y537N, Y537C, or Y537Q. In some preferred embodiments, the mutation is Y537C.

In certain embodiments, the at least one gain of function missense mutation is in the amino acid L536. In some embodiments, the mutation is L536R or L536Q.

In certain embodiments, the at least one gain of function missense mutation is in the amino acid P535. In some embodiments, the mutation is P535H.

In certain embodiments, the at least one gain of function missense mutation is in the amino acid V534. In some embodiments, the mutation is V534E.

In certain embodiments, the at least one gain of function missense mutation is in the amino acid S463. In some embodiments, the mutation is S463P.

In certain embodiments, the at least one gain of function missense mutation is in the amino acid V392. In some embodiments, the mutation is V392I.

In certain embodiments, the at least one gain of function missense mutation is in the amino acid E380. In some embodiments, the mutation is E380Q.

In some embodiments, the serum estradiol level of the patient is at least 0.35 ng/dL. In some embodiments, the serum estradiol level of the patient is about 0.30 ng/dL to about 0.35 ng/dL. In some embodiments, the serum estradiol level of the patient is about 0.25 ng/dL to about 0.30 ng/dL.

In various embodiments, lasofoxifene is administered to the selected ER$^+$ locally advanced or metastatic breast cancer patient as lasofoxifene tartrate. In various embodiments, lasofoxifene is administered by oral, intravenous, transdermal, vaginal topical, or vaginal ring administration. In certain embodiments, lasofoxifene is administered by oral administration. In some of these embodiments, lasofoxifene is administered at about 0.5 mg/day per os (p.o.) to about 10 mg/day per os. In certain embodiments, lasofoxifene is administered at about 0.5 mg/day per os to about 5 mg/day per os. In certain embodiments, lasofoxifene is administered at about 1 mg/day per os to about 5 mg/day per os. In certain embodiments, lasofoxifene is administered at about 1 mg/day per os. In certain embodiments, lasofoxifene is administered at about 5 mg/day per os. In various embodiments, lasofoxifene is administered once every day, once every two days, once every three days, once every four days, once every five days, once every six days, once every week, once every two weeks, once every three weeks, or once every month.

In certain embodiments, the method further comprises treating the patient with at least one additional endocrine therapy. In some embodiments, the patient is treated with the additional endocrine therapy at original doses. In some other embodiments, the patient is treated with the additional endocrine therapy at doses higher than original doses. In certain embodiments, the additional endocrine therapy is treatment with a selective ER modulator (SERM) other than lasofoxifene. In certain embodiments, the additional endocrine therapy is treatment with a selective ER degrader (SERD). In certain embodiments, the additional endocrine therapy is treatment with an aromatase inhibitor.

In various embodiments, the method further comprises administering to the ER$^+$ locally advanced or metastatic breast cancer patient an effective amount of cyclin-dependent kinase 4/6 (CDK4/6) inhibitor. In certain embodiments, CDK4/6 inhibitor is palbociclib, abemaciclib, or ribociclib. In some embodiments, the method further comprises administering to the patient an effective amount of mammalian target of rapamycin (mTOR) inhibitor. In certain embodiments, the mTOR inhibitor is Everolimus. In some embodiments, the method further comprises administering to the patient an effective amount of phosphoinositide 3-kinase (PI3K) inhibitor or heat shock protein 90 (HSP90) inhibitor. In some embodiments, the method further comprises administering to the patient an effective amount of human epidermal growth factor receptor 2 (HER2) inhibitor. In certain embodiments, the HER2 inhibitor is trastuzumab (Herceptin®) or ado-trastuzumab emtansine (Kadcyla®). In some embodiments, the method further comprises administering to the patient an effective amount of a histone deacetylase (HDAC) inhibitor. In some of these embodiments, the HDAC inhibitor is vorinostat (Zolinza®), romidepsin (Istodax®), chidamide (Epidaza®), panobinostat (Farydak®), belinostat (Beleodaq®, PXD101), valproic acid (Depakote®, Depakene®, Stavzor®), mocetinostat (MGCD0103), abexinostat (PCI-24781), entinostat (MS-275), pracinostat (SB939), resminostat (4SC-201), givinostat (ITF2357), quisinostat (JNJ-26481585), kevetrin, CUDC-101, AR-42, tefinostat (CHR-2835), CHR-3996, 4SC202, CG200745, rocilinostat (ACY-1215), or sulforaphane. In some embodiments, the method further comprises administering to the patient an effective amount of a checkpoint inhibitor. In some of these embodiments, the checkpoint inhibitor is an antibody specific for programmed cell death protein 1 (PD-1), programmed death-ligand 1 (PD-L1), or cytotoxic T-lymphocyte-associated protein 4 (CTLA-4). In certain embodiments, the PD-1 antibody is pembrolizumab (Keytruda®) or nivolumab (Opdivo®). In certain embodiments, the CTLA-4 antibody is ipilimumab (Yervoy®). In some embodiments, the method further comprises administering to the patient an effective amount of cancer vaccine.

In some embodiments, the patient is premenopausal. In certain embodiments, the patient has locally advanced or metastatic ER+/HER2− breast cancer. In some of these embodiments, the patient has progressed on her first hormonal treatment while on a non-steroid aromatase inhibitor (AI), fulvestrant, AI in combination with a CDK4/6 inhibitor, or fulvestrant in combination with a CDK4/6 inhibitor.

In some embodiments, the patient is perimenopausal. In certain embodiments, the patient has locally advanced or metastatic ER+/HER2− breast cancer. In some of these embodiments, the patient has progressed on her first hormonal treatment while on a non-steroid aromatase inhibitor (AI), fulvestrant, AI in combination with a CDK4/6 inhibitor, or fulvestrant in combination with a CDK4/6 inhibitor.

In some embodiments, the patient is postmenopausal. In certain embodiments, the patient has locally advanced or metastatic ER+/HER2− breast cancer. In some of these embodiments, the patient has progressed on her first hormonal treatment while on a non-steroid aromatase inhibitor (AI), fulvestrant, AI in combination with a CDK4/6 inhibitor, or fulvestrant in combination with a CDK4/6 inhibitor.

In another aspect, a method of treating primary breast cancer in women is presented. The method comprises selecting for treatment a patient who has been diagnosed with estrogen receptor positive (ER$^+$) primary breast cancer, and administering to the selected patient an effective amount of lasofoxifene, a pharmaceutically acceptable salt thereof, or a prodrug thereof.

In various embodiments, lasofoxifene is administered to the selected ER$^+$ primary breast cancer patient as lasofoxifene tartrate. In some embodiments, lasofoxifene is administered by oral, intravenous, transdermal, vaginal topical, or vaginal ring administration. In certain embodiments, lasofoxifene is administered by oral administration. In some of these embodiments, lasofoxifene is administered at about 0.5 mg/day per os to about 10 mg/day per os. In certain embodiments, lasofoxifene is administered at about 0.5 mg/day per os to about 5 mg/day per os. In certain embodiments, lasofoxifene is administered at about 1 mg/day per os to about 5 mg/day per os. In certain embodiments, lasofoxifene is administered at about 1 mg/day per os. In certain embodiments, lasofoxifene is administered at about 5 mg/day per os. In various embodiments, lasofoxifene is administered once every day, once every two days, once every three days, once every four days, once every five days, once every six days, once every week, once every two weeks, once every three weeks, or once every month.

In various embodiments, the method of treating ER+ primary breast cancer further comprises treating the patient with at least one additional endocrine therapy. In some embodiments, the patient is treated with the additional endocrine therapy at original doses. In some other embodiments, the patient is treated with the additional endocrine therapy at doses higher than original doses. In certain embodiments, the additional endocrine therapy is treatment with a selective ER modulator (SERM) other than lasofoxifene. In certain embodiments, the additional endocrine therapy is treatment with a selective ER degrader (SERD). In certain embodiments the additional endocrine therapy is treatment with an aromatase inhibitor.

In various embodiments, the method further comprises administering to the ER+ primary breast cancer patient an effective amount of cyclin-dependent kinase 4/6 (CDK4/6) inhibitor. In certain embodiments, CDK4/6 inhibitor is palbociclib, abemaciclib, or ribociclib. In some embodiments, the method further comprises administering to the patient an effective amount of mammalian target of rapamycin (mTOR) inhibitor. In certain embodiments, the mTOR inhibitor is Everolimus. In some embodiments, the method further comprises administering to the patient an effective amount of phosphoinositide 3-kinase (PI3K) inhibitor or heat shock protein 90 (HSP90) inhibitor. In some embodiments, the method further comprises administering to the patient an effective amount of human epidermal growth factor receptor 2 (HER2) inhibitor. In certain embodiments, the HER2 inhibitor is trastuzumab (Herceptin®) or ado-trastuzumab emtansine (Kadcyla®). In some embodiments, the method further comprises administering to the patient an effective amount of a histone deacetylase (HDAC) inhibitor. In some of these embodiments, the HDAC inhibitor is vorinostat (Zolinza®), romidepsin (Istodax®), chidamide (Epidaza®), panobinostat (Farydak®), belinostat (Beleodaq®, PXD101), valproic acid (Depakote®, Depakene®, Stavzor®), mocetinostat (MGCD0103), abexinostat (PCI-24781), entinostat (MS-275), pracinostat (SB939), resminostat (4SC-201), givinostat (ITF2357), quisinostat (JNJ-26481585), kevetrin, CUDC-101, AR-42, tefinostat (CHR-2835), CHR-3996, 4SC202, CG200745, rocilinostat (ACY-1215), or sulforaphane. In some embodiments, the method further comprises administering to the patient an effective amount of a checkpoint inhibitor. In some of these embodiments, the checkpoint inhibitor is an antibody specific for programmed cell death protein 1 (PD-1), programmed death-ligand 1 (PD-L1), or cytotoxic T-lymphocyte-associated protein 4 (CTLA-4). In certain embodiments, the PD-1 antibody is pembrolizumab (Keytruda®) or nivolumab (Opdivo®). In certain embodiments, the CTLA-4 antibody is ipilimumab (Yervoy®). In some embodiments, the method further comprises administering to the patient an effective amount of cancer vaccine.

In certain embodiments, the patient is premenopausal. In certain embodiments, the patient is perimenopausal. In certain embodiments, the patient is postmenopausal.

In another aspect, a method of adjuvant therapy for estrogen receptor positive (ER+) breast cancer is presented. The method comprises administering to a patient who has received primary treatment for ER+ breast cancer an effective amount of lasofoxifene, a pharmaceutically acceptable salt thereof, or a prodrug thereof, in combination with an aromatase inhibitor.

In some embodiments, lasofoxifene is administered continuously during the administration of the aromatase inhibitor. In some embodiments, lasofoxifene is administered cyclically during the administration of the aromatase inhibitor. In certain embodiments, the dosing regimen of lasofoxifene is different from the dosing regimen of the aromatase inhibitor.

In various embodiments, lasofoxifene is administered as lasofoxifene tartrate as adjuvant therapy in combination with an aromatase inhibitor. In some embodiments, the aromatase inhibitor is exemestane (Aromasin®), letrozole (Femara®), or anastrozole (Arimidex®). In some embodiments, lasofoxifene is administered by oral, intravenous, transdermal, vaginal topical, or vaginal ring administration. In certain embodiments, lasofoxifene is administered by oral administration. In some of these embodiments, lasofoxifene is administered at about 0.5 mg/day per os to about 10 mg/day per os. In certain embodiments, lasofoxifene is administered at about 0.5 mg/day per os to about 5 mg/day per os. In certain embodiments, lasofoxifene is administered at about 1 mg/day per os to about 5 mg/day per os. In certain embodiments, lasofoxifene is administered at about 1 mg/day per os. In certain embodiments, lasofoxifene is administered at about 5 mg/day per os. In various embodiments, lasofoxifene is administered once every day, once every two days, once every three days, once every four days, once every five days, once every six days, once every week, once every two weeks, once every three weeks, or once every month.

In various embodiments, the method of adjuvant therapy for estrogen receptor positive (ER+) breast cancer further comprises treating the patient with at least one additional endocrine therapy. In certain embodiments, the additional endocrine therapy is treatment with a selective ER degrader (SERD).

In various embodiments, the method of adjuvant therapy for estrogen receptor positive (ER+) breast cancer further comprises administering to the patient an effective amount of cyclin-dependent kinase 4/6 (CDK4/6) inhibitor. In certain embodiments, CDK4/6 inhibitor is palbociclib, abemaciclib, or ribociclib. In some embodiments, the method further comprises administering to the patient an effective amount of mammalian target of rapamycin (mTOR) inhibitor. In certain embodiments, the mTOR inhibitor is Everolimus. In some embodiments, the method further comprises administering to the patient an effective amount of phosphoinositide 3-kinase (PI3K) inhibitor or heat shock protein 90 (HSP90) inhibitor. In some embodiments, the method further comprises administering to the patient an effective amount of human epidermal growth factor receptor 2 (HER2) inhibitor. In certain embodiments, the HER2 inhibitor is trastuzumab (Herceptin®) or ado-trastuzumab emtansine (Kadcyla®). In some embodiments, the method further comprises administering to the patient an effective amount of a histone deacetylase (HDAC) inhibitor. In some of these embodiments, the HDAC inhibitor is vorinostat (Zolinza®), romidepsin (Istodax®), chidamide (Epidaza®), panobinostat (Farydak®), belinostat (Beleodaq®, PXD101), valproic acid (Depakote®, Depakene®, Stavzor®), mocetinostat (MGCD0103), abexinostat (PCI-24781), entinostat (MS-275), pracinostat (SB939), resminostat (4SC-201), givinostat (ITF2357), quisinostat (JNJ-26481585), kevetrin, CUDC-101, AR-42, tefinostat (CHR-2835), CHR-3996, 4SC202, CG200745, rocilinostat (ACY-1215), or sulforaphane. In some embodiments, the method further comprises administering to the patient an effective amount of a checkpoint inhibitor. In some of these embodiments, the checkpoint inhibitor is an antibody specific for programmed cell death protein 1 (PD-1), programmed death-ligand 1

(PD-L1), or cytotoxic T-lymphocyte-associated protein 4 (CTLA-4). In certain embodiments, the PD-1 antibody is pembrolizumab (Keytruda®) or nivolumab (Opdivo®). In certain embodiments, the CTLA-4 antibody is ipilimumab (Yervoy®). In some embodiments, the method further comprises administering to the patient an effective amount of cancer vaccine.

In some embodiments, lasofoxifene is administered in an amount and on a schedule sufficient to improve bone mass. In some embodiments, lasofoxifene is administered in an amount and on a schedule sufficient to improve symptoms of VVA.

In certain embodiments, the patient is premenopausal. In certain embodiments, the patient is perimenopausal. In certain embodiments, the patient is postmenopausal.

In another aspect, a method of treating cancers other than breast cancer in women is presented. The method comprises selecting for treatment a patient who has been diagnosed with estrogen receptor positive (ER$^+$) cancer, other than breast cancer, and has at least one gain of function mutations in the Estrogen Receptor 1 (ESR1) gene, and administering to the selected patient an effective amount of lasofoxifene, a pharmaceutically acceptable salt thereof, or a prodrug thereof. In some embodiments, the patient has been diagnosed with ER$^+$ ovarian cancer. In some other embodiments, the patient has been diagnosed with ER$^+$ lung cancer.

In various embodiments, lasofoxifene is administered to the selected patient with ER$^+$ cancer, other than breast cancer, as lasofoxifene tartrate. In some embodiments, lasofoxifene is administered by oral, intravenous, transdermal, vaginal topical, or vaginal ring administration. In certain embodiments, lasofoxifene is administered by oral administration. In some of these embodiments, lasofoxifene is administered at about 0.5 mg/day per os to about 10 mg/day per os. In certain embodiments, lasofoxifene is administered at about 0.5 mg/day per os to about 5 mg/day per os. In certain embodiments, lasofoxifene is administered at about 1 mg/day per os to about 5 mg/day per os. In certain embodiments, lasofoxifene is administered at about 1 mg/day per os. In certain embodiments, lasofoxifene is administered at about 5 mg/day per os. In various embodiments, lasofoxifene is administered once every day, once every two days, once every three days, once every four days, once every five days, once every six days, once every week, once every two weeks, once every three weeks, or once every month.

In various embodiments, the method of treating ER$^+$ cancer, other than breast cancer, further comprises treating the patient with at least one additional endocrine therapy. In some embodiments, the patient is treated with the additional endocrine therapy at original doses. In some other embodiments, the patient is treated with the additional endocrine therapy at doses higher than original doses. In certain embodiments, the additional endocrine therapy is treatment with a selective ER modulator (SERM) other than lasofoxifene. In certain embodiments, the additional endocrine therapy is treatment with a selective ER degrader (SERD). In certain embodiments the additional endocrine therapy is treatment with an aromatase inhibitor.

In various embodiments, the method further comprises administering to the patient with ER$^+$ cancer, other than breast cancer, an effective amount of cyclin-dependent kinase 4/6 (CDK4/6) inhibitor. In certain embodiments, CDK4/6 inhibitor is palbociclib, abemaciclib, or ribociclib. In some embodiments, the method further comprises administering to the patient an effective amount of mammalian target of rapamycin (mTOR) inhibitor. In certain embodiments, the mTOR inhibitor is Everolimus. In some embodiments, the method further comprises administering to the patient an effective amount of phosphoinositide 3-kinase (PI3K) inhibitor or heat shock protein 90 (HSP90) inhibitor. In some embodiments, the method further comprises administering to the patient an effective amount of human epidermal growth factor receptor 2 (HER2) inhibitor. In certain embodiments, the HER2 inhibitor is trastuzumab (Herceptin®) or ado-trastuzumab emtansine (Kadcyla®). In some embodiments, the method further comprises administering to the patient an effective amount of a histone deacetylase (HDAC) inhibitor. In some of these embodiments, the HDAC inhibitor is vorinostat (Zolinza®), romidepsin (Istodax®), chidamide (Epidaza®), panobinostat (Farydak®), belinostat (Beleodaq®, PXD101), valproic acid (Depakote®, Depakene®, Stavzor®), mocetinostat (MGCD0103), abexinostat (PCI-24781), entinostat (MS-275), pracinostat (SB939), resminostat (4SC-201), givinostat (ITF2357), quisinostat (JNJ-26481585), kevetrin, CUDC-101, AR-42, tefinostat (CHR-2835), CHR-3996, 4SC202, CG200745, rocilinostat (ACY-1215), or sulforaphane. In some embodiments, the method further comprises administering to the patient an effective amount of a checkpoint inhibitor. In some of these embodiments, the checkpoint inhibitor is an antibody specific for programmed cell death protein 1 (PD-1), programmed death-ligand 1 (PD-L1), or cytotoxic T-lymphocyte-associated protein 4 (CTLA-4). In certain embodiments, the PD-1 antibody is pembrolizumab (Keytruda®) or nivolumab (Opdivo®). In certain embodiments, the CTLA-4 antibody is ipilimumab (Yervoy®). In some embodiments, the method further comprises administering to the patient an effective amount of cancer vaccine.

In certain embodiments, the patient is premenopausal. In certain embodiments, the patient is perimenopausal. In certain embodiments, the patient is postmenopausal.

In another aspect, a method of treating a female patient suffering from breast cancer who is at risk of acquiring a gain of function missense mutation within the ligand binding domain (LBD) of the Estrogen Receptor 1 (ESR1) gene is presented. The method comprises administering to the female patient an effective amount of lasofoxifene, a pharmaceutically acceptable salt thereof, or a prodrug thereof.

In another aspect, a method of treating a female patient suffering from breast cancer who is at risk of acquiring resistance to endocrine therapy is presented. The endocrine therapy is optionally (i) selective ER modulator (SERM) therapy, (ii) selective ER degrader (SERD) therapy, (iii) aromatase inhibitor (AI) therapy, or (iv) any combination of (i), (ii) and/or (iii). The method comprises administering to the female patient an effective amount of lasofoxifene, a pharmaceutically acceptable salt thereof, or a prodrug thereof.

In some embodiments, the patient has primary breast cancer. In some of these embodiments, the primary breast cancer is locally advanced.

In various embodiments, the patient has been treated with endocrine therapy, optionally wherein the endocrine therapy is (i) selective ER modulator (SERM) therapy, (ii) selective ER degrader (SERD) therapy, (iii) aromatase inhibitor (AI) therapy, or (iv) any combination of (i), (ii) and/or (iii).

In another aspect, a method of treating a female patient suffering from estrogen receptor positive (ER+) primary breast cancer is presented. The method comprises administering to a female patient an effective amount of lasofoxifene, a pharmaceutically acceptable salt thereof, or a prodrug thereof.

In some embodiments, the patient is at risk of acquiring resistance to endocrine therapy, optionally wherein the endocrine therapy is (i) selective ER modulator (SERM) therapy, (ii) selective ER degrader (SERD) therapy, (iii) aromatase inhibitor (AI) therapy, or (iv) any combination of (i), (ii) and/or (iii).

In certain embodiments, the primary breast cancer is locally advanced.

In some embodiments, the patient has been treated with endocrine therapy, optionally wherein the endocrine therapy is (i) selective ER modulator (SERM) therapy, (ii) selective ER degrader (SERD) therapy, (iii) aromatase inhibitor (AI) therapy, or (iv) any combination of (i), (ii) and/or (iii).

In another aspect, a method of treating a female patient suffering from estrogen receptor positive (ER+) locally advanced or metastatic breast cancer is presented. The method comprises administering to a female patient an effective amount of lasofoxifene, a pharmaceutically acceptable salt thereof, or a prodrug thereof.

In various embodiments, the selected patient has previously been treated with one or more lines of endocrine therapy. In certain embodiments, the patient has previously been treated with a plurality of lines of endocrine therapy.

In some embodiments, the endocrine therapy that the patient has previously been treated with is a selective ER modulator (SERM). In certain embodiments, the SERM is tamoxifen, raloxifene, bazedoxifene, toremifene, or ospemifene.

In some embodiments, the endocrine therapy that the patient has previously been treated with is a selective ER degrader (SERD). In certain embodiments, the SERD is fulvestrant, RAD1901, ARN-810 (GDC-0810), or AZD9496.

In some embodiments, the endocrine therapy that the patient has previously been treated with is an aromatase inhibitor. In certain embodiments, the aromatase inhibitor is exemestane (Aromasin®), letrozole (Femara®), or anastrozole (Arimidex®).

In some embodiments, the patient has disease progression after endocrine therapy. In some embodiments, the patient is resistant to endocrine therapy.

In various embodiments, the patient's cancer has at least one gain of function missense mutation within the ligand binding domain (LBD) of the Estrogen Receptor 1 (ESR1) gene. In some embodiments, the patient has previously been determined to have at least one gain of function missense mutation within the ligand binding domain (LBD) of the Estrogen Receptor 1 (ESR1) gene. In certain embodiments, the method further comprises the earlier step of: determining that the patient has at least one gain of function missense mutation within the ligand binding domain (LBD) of the Estrogen Receptor 1 (ESR1) gene.

In some embodiments, the at least one of gain of function missense mutation is in any one of amino acids D538, Y537, L536, P535, V534, S463, V392, or E380.

In certain embodiments, the at least one gain of function missense mutation is in the amino acid D538. In some preferred embodiments the mutation is D538G.

In certain embodiments, the at least one gain of function missense mutation is in the amino acid Y537. In some embodiments, the mutation is Y537S, Y537N, Y537C, or Y537Q. In some preferred embodiments, the mutation is Y537C.

In certain embodiments, the at least one gain of function missense mutation is in the amino acid L536. In some embodiments, the mutation is L536R or L536Q.

In certain embodiments, the at least one gain of function missense mutation is in the amino acid P535. In some embodiments, the mutation is P535H.

In certain embodiments, the at least one gain of function missense mutation is in the amino acid V534. In some embodiments, the mutation is V534E.

In certain embodiments, the at least one gain of function missense mutation is in the amino acid S463. In some embodiments, the mutation is S463P.

In certain embodiments, the at least one gain of function missense mutation is in the amino acid V392. In some embodiments, the mutation is V392I.

In certain embodiments, the at least one gain of function missense mutation is in the amino acid E380. In some embodiments, the mutation is E380Q.

In various embodiments, lasofoxifene is administered to the selected $ER^+$ locally advanced or metastatic breast cancer patient as lasofoxifene tartrate. In various embodiments, lasofoxifene is administered by oral, intravenous, transdermal, vaginal topical, or vaginal ring administration. In certain embodiments, lasofoxifene is administered by oral administration. In some of these embodiments, lasofoxifene is administered at about 0.5 mg/day per os (p.o.) to about 10 mg/day per os. In certain embodiments, lasofoxifene is administered at about 0.5 mg/day per os to about 5 mg/day per os. In certain embodiments, lasofoxifene is administered at about 1 mg/day per os to about 5 mg/day per os. In certain embodiments, lasofoxifene is administered at about 1 mg/day per os. In certain embodiments, lasofoxifene is administered at about 5 mg/day per os. In various embodiments, lasofoxifene is administered once every day, once every two days, once every three days, once every four days, once every five days, once every six days, once every week, once every two weeks, once every three weeks, or once every month.

In certain embodiments, the method further comprises treating the patient with at least one additional endocrine therapy. In some embodiments, the patient is treated with the additional endocrine therapy at original doses. In some other embodiments, the patient is treated with the additional endocrine therapy at doses higher than original doses. In certain embodiments, the additional endocrine therapy is treatment with a selective ER modulator (SERM) other than lasofoxifene. In certain embodiments, the additional endocrine therapy is treatment with a selective ER degrader (SERD). In certain embodiments, the additional endocrine therapy is treatment with an aromatase inhibitor.

In various embodiments, the method further comprises administering to the $ER^+$ locally advanced or metastatic breast cancer patient an effective amount of cyclin-dependent kinase 4/6 (CDK4/6) inhibitor. In certain embodiments, CDK4/6 inhibitor is palbociclib, abemaciclib, or ribociclib. In some embodiments, the method further comprises administering to the patient an effective amount of mammalian target of rapamycin (mTOR) inhibitor. In certain embodiments, the mTOR inhibitor is Everolimus. In some embodiments, the method further comprises administering to the patient an effective amount of phosphoinositide 3-kinase (PI3K) inhibitor or heat shock protein 90 (HSP90) inhibitor. In some embodiments, the method further comprises administering to the patient an effective amount of human epidermal growth factor receptor 2 (HER2) inhibitor. In certain embodiments, the HER2 inhibitor is trastuzumab (Herceptin®) or ado-trastuzumab emtansine (Kadcyla®). In some embodiments, the method further comprises administering to the patient an effective amount of a histone deacetylase (HDAC) inhibitor. In some of these embodiments, the HDAC inhibitor is vorinostat (Zolinza®), romidepsin (Istodax®), chidamide (Epidaza®), panobinostat (Farydak®), belinostat (Beleodaq®, PXD101), valproic acid (Depakote®, Depakene®, Stavzor®), mocetinostat (MGCD0103), abexinostat (PCI-24781), entinostat (MS-275), pracinostat (SB939), resminostat (4SC-201), givinostat (ITF2357), quisinostat (JNJ-26481585), kevetrin, CUDC-101, AR-42, tefinostat (CHR-2835), CHR-3996, 4SC202, CG200745, rocilinostat (ACY-1215), or sulforaphane. In some embodiments, the method further comprises administering to the patient an effective amount of a checkpoint inhibitor. In some of these embodiments, the checkpoint inhibitor is an antibody specific for programmed cell death protein 1 (PD-1), programmed death-ligand 1 (PD-L1), or cytotoxic T-lymphocyte-associated protein 4 (CTLA-4). In certain embodiments, the PD-1 antibody is pembrolizumab (Keytruda®) or nivolumab (Opdivo®). In certain embodiments, the CTLA-4 antibody is ipilimumab (Yervoy®). In some embodiments, the method further comprises administering to the patient an effective amount of cancer vaccine.

In some embodiments, the patient is premenopausal. In certain embodiments, the patient has locally advanced or metastatic ER+/HER2− breast cancer. In some of these embodiments, the patient has progressed on her first hormonal treatment while on a non-steroid aromatase inhibitor (AI), fulvestrant, AI in combination with a CDK4/6 inhibitor, or fulvestrant in combination with a CDK4/6 inhibitor.

In some embodiments, the patient is perimenopausal. In certain embodiments, the patient has locally advanced or metastatic ER+/HER2− breast cancer. In some of these embodiments, the patient has progressed on her first hormonal treatment while on a non-steroid aromatase inhibitor (AI), fulvestrant, AI in combination with a CDK4/6 inhibitor, or fulvestrant in combination with a CDK4/6 inhibitor.

In some embodiments, the patient is postmenopausal. In certain embodiments, the patient has locally advanced or metastatic ER+/HER2− breast cancer. In some of these embodiments, the patient has progressed on her first hormonal treatment while on a non-steroid aromatase inhibitor (AI), fulvestrant, AI in combination with a CDK4/6 inhibitor, or fulvestrant in combination with a CDK4/6 inhibitor.

5. BRIEF DESCRIPTION OF THE DRAWINGS

These and other features, aspects, and advantages of the present invention will become better understood with regard to the following description, and accompanying drawings, where:

6. DETAILED DESCRIPTION OF THE INVENTION

Figure 1A:
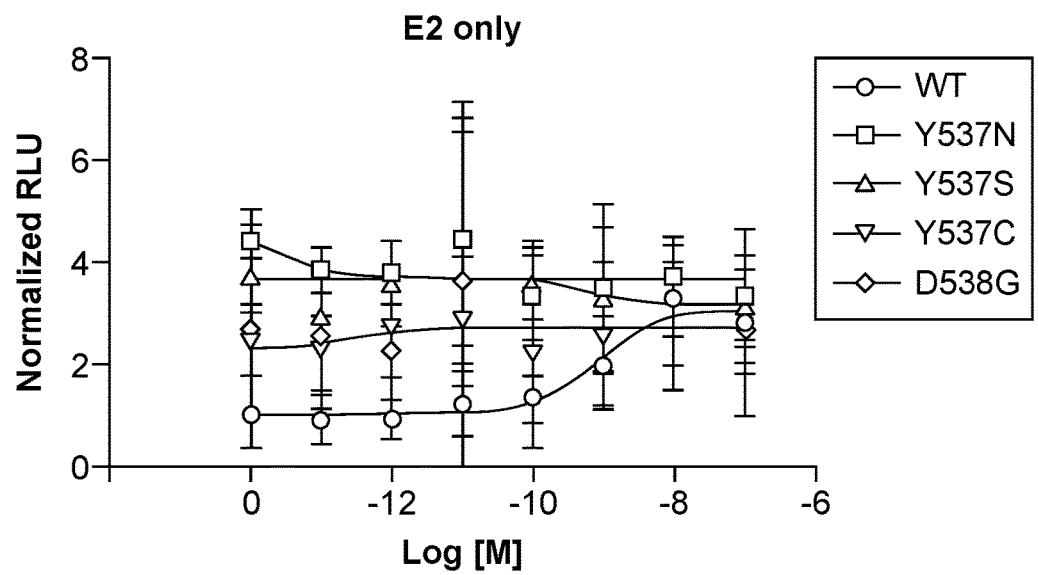
FIG. 1A and FIG. 1B show the effects of lasofoxifene on ESR1 ligand binding domain ("LBD") mutations in Caov2 ovarian carcinoma cells, with FIG. 1A demonstrating that the mutant receptors are constitutively active and do not respond to 17-β estradiol ("E2"), and FIG. 1B demonstrating that lasofoxifene inhibits the mutant receptor activity in a dose-response manner.

Endocrine therapy is often used for treatment and prevention of ER+ breast cancers. Different types of endocrine therapy include selective ER modulators (SERMs), such as tamoxifen; selective ER degraders (SERDs), such as fulvestrant; and aromatase inhibitors (AIs). Although endocrine therapy has led to a significant improvement in outcome for women with ER+ breast cancer, its effectiveness is limited by intrinsic and acquired endocrine resistance. Recent studies on the mechanism of endocrine resistance have demonstrated that in some cases Estrogen Receptor 1 (ESR1) gene mutations lead to the conformational change of the ERα protein towards a constitutively active state and result in ligand-independent activity that is relatively resistant to tamoxifen, fulvestrant, and estrogen deprivation. See Jeselsohn et al., *Clinical Cancer Research* 20(7): 1757-1767 (2014).

Lasofoxifene is a nonsteroidal selective ER modulator (SERM). It has high binding affinity for the estrogen receptor and acts as a tissue-selective estrogen agonist or antagonist. In the double-blind, placebo-controlled, randomized Postmenopausal Evaluation and Risk-Reduction with Lasofoxifene (PEARL) trial, lasofoxifene was found to reduce the risk of osteoporosis. See Cummings et al., *The New England Journal of Medicine* 326(8): 686-696 (2010). In the PEARL trial, it was also found that lasofoxifene reduced the risk of breast cancer in post-menopausal women with osteoporosis. See LaCroix et al., *Journal of the National Cancer Institute* 102(22): 1706-1715 (2010). However, the effect of lasofoxifene as a treatment for breast cancer, and its effect on cancers with endocrine resistance, has not previously been determined.

Using cell lines with engineered mutations in the ESR1 gene, we discovered that lasofoxifene inhibits the mutant receptor activity in a dose-responsive manner at concentrations that can be achieved clinically, newly making possible methods of treating ER+ locally advanced or metastatic breast cancer, ER+ primary breast cancer, and other ER+ cancers, including cancers having ESR1 mutations, using lasofoxifene, whose effectiveness is not precluded by endocrine resistance.

6.1. Methods of Treatment

Accordingly, in a first aspect, disclosed herein are methods of treating cancers in women, comprising selecting for treatment a patient who has been diagnosed with estrogen receptor positive (ER+) cancer. The selected patient is treated with an effective amount of lasofoxifene, a pharmaceutically acceptable salt thereof, or a prodrug thereof.

6.1.1. Patient with ER+ Cancer

In various embodiments, the patient has been diagnosed with ER+ cancer by immunohistochemistry (IHC) performed on a sample of the patient's cancer. In some embodiments, the patient has been diagnosed with locally advanced or metastatic ER+ breast cancer. In some embodiments, the patient has been diagnosed with ER+ primary breast cancer. In some embodiments, the patient has been diagnosed with an ER+ cancer other than breast cancer. In some of these embodiments, the patient has been diagnosed with ER+ ovarian cancer. In some of these embodiments, the patient has been diagnosed with ER+ lung cancer.

In some embodiments, cells of the patient's cancer have acquired a gain of function missense mutation within the ligand binding domain (LBD) of the Estrogen Receptor 1 (ESR1) gene.

In some embodiments, the patient is at risk of acquiring resistance to endocrine therapy. In particular embodiments, the patient is at risk of acquiring resistance to endocrine therapy due to the increased expression of estrogen receptor. In particular embodiments, the patient is at risk of acquiring resistance to endocrine therapy due to the increased expression of co-activators of estrogen receptor. In particular embodiments, the patient is at risk of acquiring resistance to endocrine therapy due to increased phosphorylation level and activity of estrogen receptor and its co-activators. In particular embodiments, the patient is at risk of acquiring resistance to endocrine therapy due to change of tumor microenvironment and other host related factors. In some preferred embodiments, the patient is at risk of acquiring resistance to endocrine therapy due to mutations in the Estrogen Receptor 1 (ESR1) gene.

In some of these embodiments, the endocrine therapy to which the patient is at risk of acquiring resistance is (i) selective ER modulator (SERM) therapy, (ii) selective ER degrader (SERD) therapy, (iii) aromatase inhibitor therapy (AI), or (iv) any combination of (i), (ii) and/or (iii).

6.1.2. Previous Treatment with Endocrine Therapy

In various embodiments, the ER+ cancer patient has previously been treated with one or more lines of endocrine therapy. In certain embodiments, the patient has previously been treated with one line of endocrine therapy. In certain other embodiments, the patient has previously been treated with a plurality of lines of endocrine therapy. In some embodiments, the patient has previously been treated with two lines of endocrine therapy. In some embodiments, the patient has previously been treated with three lines of endocrine therapy. In some embodiments, the patient has previously been treated with four or more lines of endocrine therapy.

In some embodiments, the endocrine therapy that the patient has previously been treated with is a selective ER modulator (SERM). In some embodiments, the selective ER modulator is selected from tamoxifen, raloxifene, bazedoxifene, toremifene, and ospemifene. In certain embodiments, the selective ER modulator is tamoxifen.

In some embodiments, the endocrine therapy that the patient has previously been treated with is a selective ER degrader (SERD). In various embodiments, the selective ER degrader binds to the estrogen receptor and leads to the proteasomal degradation of the receptor. In some embodiments, the selective ER degrader is selected from fulvestrant, RAD1901, ARN-810 (GDC-0810), and AZD9496. In certain embodiments, the selective ER degrader is fulvestrant.

In some embodiments, the endocrine therapy with which the patient has previously been treated is an aromatase inhibitor (AI). In various embodiments, the aromatase inhibitor blocks the production of estrogen. In some embodiments, the aromatase inhibitor is selected from exemestane (Aromasin®), letrozole (Femara®), and anastrozole (Arimidex®).

In some embodiments, the endocrine therapy that the patient has previously been treated with is ovarian suppression. In certain embodiments, ovarian suppression is achieved by oophorectomy. In certain embodiments, ovarian suppression is achieved by administration of a GnRH antagonist.

In certain embodiments, the patient's cancer has relapsed or progressed after the previous endocrine therapy treatment. In some embodiments, the patient's cancer has relapsed or progressed after tamoxifen treatment. In some embodiments, the patient's cancer has relapsed or progressed after fulvestrant treatment. In some embodiments, the patient's cancer has relapsed or progressed after aromatase inhibitor treatment. In some of these embodiments, the patient's cancer has relapsed or progressed after multiple lines of endocrine therapy treatment.

In some embodiments, the ER+ cancer patient has not been treated previously with endocrine therapy.

In certain embodiments, the patient is resistant to endocrine therapy other than lasofoxifene. In some embodiments, the patient has intrinsic endocrine resistance. In some embodiments, the patient has acquired endocrine resistance. In particular embodiments, the patient is resistant to endocrine therapy due to the increased expression of estrogen receptor. In particular embodiments, the patient is resistant to endocrine therapy due to the increased expression of co-activators of estrogen receptor. In particular embodiments, the patient is resistant to endocrine therapy due to increased phosphorylation level and activity of estrogen receptor and its co-activators. In particular embodiments, the patient is resistant to endocrine therapy due to change of tumor microenvironment and other host related factors. In some preferred embodiments, the patient is resistant to endocrine therapy due to gene mutations in the Estrogen Receptor 1 (ESR1) gene.

In various embodiments, the patient is resistant to clinical doses of one or more SERMs other than lasofoxifene. In some of these embodiments, the patient is resistant to clinical doses of tamoxifen. In various embodiments, the patient is resistant to clinical doses of one or more SERDs. In some of these embodiments, the patient is resistant to clinical doses of fulvestrant. In various embodiments, the patient is resistant to clinical doses of one or more aromatase inhibitors. In various embodiments, the patient is resistant to higher than clinical doses of one or more SERMs other than lasofoxifene. In some of these embodiments, the patient is resistant to higher than clinical doses of tamoxifen. In various embodiments, the patient is resistant to higher than clinical doses of one or more SERDs. In some of these embodiments, the patient is resistant to higher than clinical doses of fulvestrant. In various embodiments, the patient is resistant to higher than clinical doses of one or more aromatase inhibitors.

In certain embodiments, the ER+ cancer patient has not been demonstrated to have endocrine resistance. In some of these embodiments, the patient has not been demonstrated to have endocrine resistance due to the limitations of the detection methods.

In some embodiments, lasofoxifene is administered to the ER+ cancer patient after completion of cancer treatment. In some of these embodiments, lasofoxifene is administered to the patient to treat occult micrometastasis.

6.1.3. Menopause Status

In some embodiments, the ER+ cancer patient is premenopausal. In specific embodiments, the patient is premenopausal and has locally advanced or metastatic ER+ cancer. In particular embodiments, the patient is premenopausal and has locally advanced or metastatic ER+ breast cancer.

In certain embodiments, the ER+ cancer patient is perimenopausal. In specific embodiments, the patient is perimenopausal and has locally advanced or metastatic ER+ cancer. In particular embodiments, the patient is perimenopausal and has locally advanced or metastatic ER+ breast cancer.

In typical embodiments, the ER+ cancer patient is postmenopausal. In specific embodiments, the patient is postmenopausal and has locally advanced or metastatic ER+ cancer. In particular embodiments, the patient is postmenopausal and has locally advanced or metastatic ER+ breast cancer.

In certain embodiments, lasofoxifene is administered to a premenopausal woman with locally advanced or metastatic ER+/HER2− breast cancer. In certain embodiments, lasofoxifene is administered to a premenopausal woman with locally advanced or metastatic ER+/HER2− breast cancer who has progressed while on her first hormonal treatment with a non-steroid aromatase inhibitor (AI), fulvestrant, AI in combination with a CDK4/6 inhibitor, or fulvestrant in combination with a CDK4/6 inhibitor.

In certain embodiments, lasofoxifene is administered to a perimenopausal woman with locally advanced or metastatic ER+/HER2− breast cancer. In certain embodiments, lasofoxifene is administered to a perimenopausal woman with locally advanced or metastatic ER+/HER2− breast cancer who has progressed while on her first hormonal treatment with a non-steroid aromatase inhibitor (AI), fulvestrant, AI in combination with a CDK4/6 inhibitor, or fulvestrant in combination with a CDK4/6 inhibitor.

In certain embodiments, lasofoxifene is administered to a postmenopausal woman with locally advanced or metastatic ER+/HER2− breast cancer. In certain embodiments, lasofoxifene is administered to a postmenopausal woman with locally advanced or metastatic ER+/HER2− breast cancer who has progressed while on her first hormonal treatment with on a non-steroid aromatase inhibitor (AI), fulvestrant, AI in combination with a CDK4/6 inhibitor, or fulvestrant in combination with a CDK4/6 inhibitor.

6.1.4. Mutations in ESR1 Gene

In various embodiments, the patient has an ER+ cancer, cells of which have at least one mutation in the Estrogen Receptor 1 (ESR1) gene, which encodes the Estrogen Receptor α (ERα) protein. In some embodiments, the mutation leads to the ligand-independent activity of the estrogen receptor. In some embodiments, the mutation leads to enhanced ligand stimulated activity of estrogen receptor. In some embodiments, the mutation leads to resistance to endocrine therapy. In some embodiments, the mutation promotes tumor growth. In some embodiments, the mutation enhances metastatic activity of cancer. In some preferred embodiments, the mutation enhances metastatic activity of ER+ metastatic breast cancer.

In some embodiments, the mutation arises from a rare and undetectable pre-existing clone. In some embodiments, the mutation is acquired de novo during the course of endocrine therapy treatment. In some preferred embodiments, the mutation is acquired de novo during the course of endocrine therapy treatment of breast cancer. In some embodiments, the mutation is acquired de novo after multiple lines of endocrine therapy treatment. In some embodiments, the mutation is acquired de novo after multiple lines of endocrine therapy treatment of metastatic breast cancer. In various embodiments, the mutant clone expands to become a more dominant clone over the course of successive lines of endocrine therapy.

In some embodiments, the mutation in the ESR1 gene is missense point mutation. In some embodiments, the mutation in the ESR1 gene is truncating mutation. In some embodiments, the mutation in the ESR1 gene is gene amplification. In some embodiments, the mutation in the ESR1 gene is genomic rearrangement.

In some preferred embodiments, the patient has an ER+ cancer that has at least one gain of function missense mutation within the ligand binding domain (LBD) of the ESR1 gene. In various embodiments, at least one of the mutations is in an amino acid selected from D538, Y537, L536, P535, V534, S463, V392, and E380. (The amino acids are numbered according to the ESR1 protein with the NCBI accession number NP_000116.2.)

In particular embodiments, the mutation increases the stability of the agonist conformation of Helix 12 of the ERα protein. In some of these embodiments, the mutation increases the binding of the estrogen receptor to its co-activators. In some of these embodiments, the mutation leads to hormone independent activity of estrogen receptor. In some of these embodiments, the mutation leads to resistance to tamoxifen, fulvestrant, and/or aromatase inhibitors.

In certain embodiments, the mutation is in the amino acid D538. In certain preferred embodiments, the mutation is D538G.

In certain embodiments, the mutation is in the amino acid Y537. In some of these embodiments, the mutation is Y537S, Y537N, Y537C, or Y537Q. In certain preferred embodiments, the mutation is Y537C.

In some embodiments, the mutation is in the amino acid L536. In certain embodiments, the mutation is L536R or L536Q.

In some embodiments, the mutation is in the amino acid P535. In certain embodiments, the mutation is P535H.

In some embodiments, the mutation is in the amino acid V534. In certain embodiments, the mutation is V534E.

In some embodiments, the mutation is in the amino acid S463. In certain embodiments, the mutation is S463P.

In some embodiments, the mutation is in the amino acid V392. In certain embodiments, the mutation is V392I.

In some embodiments, the mutation is in the amino acid E380. In certain embodiments, the mutation is E380Q.

6.1.4.1. Detection of the ESR1 Gene Mutations

In various embodiments, the patient has been previously determined to have at least one mutation in the ESR1 gene. Some embodiments of the methods described herein further include the step of detecting the mutations in ESR1 gene.

In some embodiments, massively parallel next generation sequencing (NGS) is used for detecting the estrogen receptor mutations in the patient's cancer. In certain embodiments, the entire genome is sequenced. In certain embodiments, selected gene panels of cancer-related genes are sequenced. In certain embodiments, all coding exons within a given set of genes are sequenced. In certain embodiments, known "hotspot" regions within a given set of genes are sequenced. However, the inherent error rate of current next generation sequencing techniques is up to 1%, limiting the sensitivity and specificity of detection. In some embodiments, targeted sequencing is used for detecting the presence of the ESR1 mutations. Although targeted sequencing allows deeper sequencing, it is also currently limited by the 1% error rate. In some embodiments, methods with reduced sequencing error rate are used. In a particular embodiment, Safe-Sequencing System (Safe-SeqS) is used, which tags each template molecule to allow for confident identification of rare variants. See Kinde et al., *Proceedings of the National Academy of Sciences* 108(23): 9530-9535 (2011). In particular embodiments, ultrasensitive Duplex sequencing is used, which independently tags and sequences each of the two strands of a DNA duplex. See Schmitt et al., *Proceed-*

*ings of the National Academy of Sciences* 109(36): 14508-14513 (2012). In some embodiments, digital droplet PCR is used, which emulsifies DNA in thousands to millions of droplets to encapsulate single DNA molecules, designed with mutant specific primers. See Vogelstein and Kinzler, *Proceedings of the National Academy of Sciences* 96(16): 2322-2326 (1999) and Huggett et al., *Clinical Chemistry* 61(1): 79-88 (2014).

In some embodiments, the detection of the ESR1 mutations takes place at the initial diagnosis. In some embodiments, the detection of the mutations takes place at the time of disease progression, relapse, or recurrence. In some embodiments, the detection of the mutations takes place at the time of disease progression. In some embodiments, the detection of the mutations takes place at the time when the disease is stable.

In some embodiments, one or more tissue specimens are obtained for detection of the mutations. In certain embodiments, the tissue specimen is a tumor biopsy. In certain embodiments, the tissue specimen is a biopsy of metastases. In some other embodiments, liquid biopsies are obtained for detection of the mutations. In certain embodiments, the liquid biopsy is circulating tumor cells (CTCs). In certain other embodiments, the liquid biopsy is cell-free DNA from blood samples.

In specific embodiments, the ESR1 mutations are monitored by circulating tumor DNA (ctDNA) analysis. In some embodiments, the ctDNA analysis is performed throughout the course of treatment. In some of these embodiments, the ctDNA is extracted from patient blood samples. In certain embodiments, the ctDNA is evaluated by digital PCR analysis of the ESR1 mutations.

6.1.5. Estradiol Levels

In various embodiments, the patient selected for treatment based on presence of ESR1 gene mutations is further selected based on serum estradiol level.

In certain embodiments, the serum estradiol level of the patient with the ER$^+$ cancer having an ESR1 gene mutation is at least 0.20 ng/dL, such as at least 0.25 ng/dL, at least 0.30 ng/dL, at least 0.35 ng/dL, at least 0.40 ng/dL, at least 0.45 ng/dL, at least 0.50 ng/dL, at least 0.55 ng/dL, at least 0.60 ng/dL, at least 0.65 ng/dL, at least 0.70 ng/dL, at least 0.75 ng/dL, at least 0.80 ng/dL, at least 0.85 ng/dL, at least 0.90 ng/dL, at least 0.95 ng/dL, or at least 1.0 ng/dL.

In certain embodiments, the serum estradiol level of the patient with the ESR1 gene mutation is about 0.20 ng/dL to about 1.0 ng/dL, such as about 0.20 ng/dL to about 0.25 ng/dL, about 0.25 ng/dL to about 0.30 ng/dL, about 0.30 ng/dL to about 0.35 ng/dL, about 0.35 ng/dL to about 0.40 ng/dL, about 0.40 ng/dL to about 0.45 ng/dL, about 0.45 ng/dL to about 0.50 ng/dL, about 0.50 ng/dL to about 0.55 ng/dL, about 0.55 ng/dL to about 0.60 ng/dL, about 0.60 ng/dL to about 0.65 ng/dL, about 0.65 ng/dL to about 0.70 ng/dL, about 0.70 ng/dL to about 0.75 ng/dL, about 0.75 ng/dL to about 0.80 ng/dL, about 0.80 ng/dL to about 0.85 ng/dL, about 0.85 ng/dL to about 0.90 ng/dL, about 0.90 ng/dL to about 0.95 ng/dL, about 0.95 ng/dL to about 1.0 ng/dL.

6.1.6. Adjuvant Treatment

In various embodiments, lasofoxifene is administered to the patient as adjuvant treatment. In certain embodiments, lasofoxifene is administered to the patient as adjuvant treatment alone. In certain other embodiments, lasofoxifene is administered to the patient as adjuvant treatment in combination with other endocrine therapies. In some embodiments, lasofoxifene is administered to the patient after the primary treatment. In some of these embodiments, lasofoxifene is administered to the patient after surgical removal or debulking of the cancer.

In some embodiments, lasofoxifene is administered to the patient as adjuvant therapy in combination with an aromatase inhibitor (AI). In various embodiments, the aromatase inhibitor is exemestane (Aromasin®), letrozole (Femara®), or anastrozole (Arimidex®).

In various embodiments, the aromatase inhibitor predisposes the patient to bone-related toxic effects. In some embodiments, the aromatase inhibitor predisposes the patient to osteoporosis. In some embodiments, the aromatase inhibitor predisposes the patient to bone loss. In some embodiments, the aromatase inhibitor predisposes the patient to bone fractures. In some embodiments, the aromatase inhibitor predisposes the patient to bone pain.

In various embodiments, the aromatase inhibitor predisposes the patient to vulvovaginal atrophy (VVA).

In some embodiments, lasofoxifene is administered continuously during the administration of the aromatase inhibitor. In some other embodiments, lasofoxifene is administered cyclically during the administration of the aromatase inhibitor. In some embodiments, lasofoxifene and the aromatase inhibitor are administered together (simultaneously). In some other embodiments, lasofoxifene and the aromatase inhibitor are administered separately (sequentially).

In certain embodiments, the dosing regimen of lasofoxifene is different from the dosing regimen of the aromatase inhibitor. In some of these embodiments, the dosing quantity of lasofoxifene is different from the dosing quantity of the aromatase inhibitor. In some embodiments, the dosing schedule of lasofoxifene is different from the dosing schedule of the aromatase inhibitor. In some embodiments, the route of administration of lasofoxifene is different from the route of administration of the aromatase inhibitor.

In certain embodiments, the dosing regimen of lasofoxifene is the same as the dosing regimen of the aromatase inhibitor. In some embodiments, the dosing quantity of lasofoxifene is the same as the dosing quantity of the aromatase inhibitor. In some embodiments, the dosing schedule of lasofoxifene is the same as the dosing schedule of the aromatase inhibitor. In some embodiments, the route of administration of lasofoxifene is the same as the route of administration of the aromatase inhibitor.

In some embodiments, lasofoxifene is administered as adjuvant therapy in combination with an aromatase inhibitor to the patient for one year. In some embodiments, lasofoxifene is administered as adjuvant therapy in combination with an aromatase inhibitor to the patient for two years. In some embodiments, lasofoxifene is administered as adjuvant therapy in combination with an aromatase inhibitor to the patient for three years. In some embodiments, lasofoxifene is administered as adjuvant therapy in combination with an aromatase inhibitor to the patient for four years. In some embodiments, lasofoxifene is administered as adjuvant therapy in combination with an aromatase inhibitor to the patient for five years. In some embodiments, lasofoxifene is administered as adjuvant therapy in combination with an aromatase inhibitor to the patient for six years. In some embodiments, lasofoxifene is administered as adjuvant therapy in combination with an aromatase inhibitor to the patient for seven years. In some embodiments, lasofoxifene is administered as adjuvant therapy in combination with an aromatase inhibitor to the patient for eight years. In some embodiments, lasofoxifene is administered as adjuvant therapy in combination with an aromatase inhibitor to the patient for nine years. In some embodiments, lasofoxifene is administered as adjuvant therapy in combination with an aromatase inhibitor to the patient for ten years. In some other embodiments, lasofoxifene is administered as adjuvant therapy in combination with an aromatase inhibitor to the patient for more than ten years. In certain embodiments, lasofoxifene is administered as adjuvant therapy in combination with an aromatase inhibitor until the patient's cancer progresses on therapy.

In some embodiments, lasofoxifene is administered as adjuvant therapy in combination with an aromatase inhibitor to increase the disease-free survival of the breast cancer patient. In some embodiments, lasofoxifene is administered as adjuvant therapy in combination with an aromatase inhibitor to decrease the incidence of contralateral breast cancer. In some embodiments, lasofoxifene is administered as adjuvant therapy in combination with an aromatase inhibitor to prevent the recurrence or progression of the cancer.

6.2. Lasofoxifene

In various embodiments, the selected patient is treated with an effective amount of lasofoxifene, a pharmaceutically acceptable salt thereof, or a prodrug thereof. In some preferred embodiments, lasofoxifene is administered to the selected patient as lasofoxifene tartrate.

The term "pharmaceutically acceptable salt" refers to non-toxic pharmaceutically acceptable salts. See Gould, *International Journal of Pharmaceutics* 33: 201-217 (1986) and Berge et al., *Journal of Pharmaceutical Sciences* 66(1): 1-19 (1977). Other salts well known to those in the art may, however, be used. Representative organic or inorganic acids include, but are not limited to, hydrochloric, hydrobromic, hydriodic, perchloric, sulfuric, nitric, phosphoric, acetic, propionic, glycolic, lactic, succinic, maleic, fumaric, malic, tartaric, citric, benzoic, mandelic, methanesulfonic, hydroxyethanesulfonic, benzenesulfonic, oxalic, pamoic, 2-naphthalenesulfonic, p-toluenesulfonic, cyclohexanesulfamic, salicylic, saccharinic or trifluoroacetic acid. Representative organic or inorganic bases include, but are not limited to, basic or cationic salts such as benzathine, chloroprocaine, choline, diethanolamine, ethylenediamine, meglumine, procaine, aluminum, calcium, lithium, magnesium, potassium, sodium and zinc.

Embodiments also include prodrugs of the compounds disclosed herein. In general, such prodrugs will be functional derivatives of the compounds which are readily convertible in vivo into the required compound. Thus, in the methods of treatment of the present invention, the term "administering" shall encompass the treatment of the various disorders described with the compound specifically disclosed or with a compound which may not be specifically disclosed, but which converts to the specified compound in vivo after administration to the subject. Conventional procedures for the selection and preparation of suitable prodrug derivatives are described, for example, in *"Design of Prodrugs"*, H. Bundgaard, Elsevier, 1985.

Some of the crystalline forms for the compounds may exist as polymorphs and as such are intended to be included in the present invention. In addition, some of the compounds may form solvates with water (i.e., hydrates) or common organic solvents, and such solvates are intended to be encompassed by some embodiments.

Where the processes for the preparation of the compounds as disclosed herein give rise to mixtures of stereoisomers, these isomers may be separated by conventional techniques such as preparative chromatography. The compounds may be prepared in racemic form or as individual enantiomers or diastereomers by either stereospecific synthesis or by resolution. The compounds may, for example, be resolved into their component enantiomers or diastereomers by standard techniques, such as the formation of stereoisomeric pairs by salt formation with an optically active base, followed by fractional crystallization and regeneration of the free acid. The compounds may also be resolved by formation of stereoisomeric esters or amides, followed by chromatographic separation and removal of the chiral auxiliary. Alternatively, the compounds may be resolved using a chiral HPLC column. It is to be understood that all stereoisomers, racemic mixtures, diastereomers, cis-trans isomers, and enantiomers thereof are encompassed by some embodiments.

6.3. Pharmaceutical Compositions

Methods for treatment of estrogen receptor positive ($ER^+$) cancers include administering a therapeutically effective amount of lasofoxifene, a pharmaceutically acceptable salt thereof, or a prodrug thereof. The lasofoxifene, the pharmaceutically acceptable salt, or the prodrug of the invention can be formulated in pharmaceutical compositions. In addition to lasofoxifene, a pharmaceutically acceptable salt thereof, or a prodrug thereof, the composition further comprises a pharmaceutically acceptable excipient, carrier, buffer, stabilizer or other materials well known to those skilled in the art. Such materials should be non-toxic and should not interfere with the efficacy of the active ingredient. The precise nature of the carrier or other material can depend on the route of administration, e.g. oral, intravenous, transdermal, vaginal topical, or vaginal ring.

Pharmaceutical compositions for oral administration can be in tablet, capsule, powder or liquid form. A tablet can include a solid carrier such as gelatin or an adjuvant. Liquid pharmaceutical compositions generally include a liquid carrier such as water, petroleum, animal oil, vegetable oil, mineral oil or synthetic oil. Physiological saline solution, dextrose or other saccharide solution or glycols such as ethylene glycol, propylene glycol or polyethylene glycol can also be included.

For parenteral administration, the lasofoxifene will be in the form of a parenterally acceptable aqueous solution which is pyrogen-free and has suitable pH, isotonicity and stability. Those of relevant skill in the art are well able to prepare suitable solutions using, for example, isotonic vehicles such as Sodium Chloride Injection, Ringer's Injection, Lactated Ringer's Injection. Preservatives, stabilizers, buffers, antioxidants and/or other additives can be included, as required.

Pharmaceutical compositions for vaginal topical administration can be in the form of ointment, cream, gel or lotion. The pharmaceutical compositions for vaginal topical administration often include water, alcohol, animal oil, vegetable oil, mineral oil or synthetic oil. Hydrocarbon (paraffin), wool fat, beeswax, macrogols, emulsifying wax or cetrimide can also be included.

A composition can be administered alone or in combination with other treatments, either simultaneously or sequentially, dependent upon the condition to be treated.

6.4. Treatment Regimens

In the methods of administering an effective amount of lasofoxifene in the form of a pharmaceutical composition as described above for treatment of $ER^+$ cancer, the terms "treatment", "treating", and the like are used herein to generally mean obtaining a desired pharmacologic and/or physiologic effect. The effect may be prophylactic, in terms of completely or partially preventing a disease, condition, or symptoms thereof, and/or may be therapeutic in terms of a partial or complete cure for a disease or condition and/or adverse effect, such as a symptom, attributable to the disease or condition. "Treatment" as used herein covers any treatment of a disease or condition of a mammal, particularly a human, and includes: (a) preventing the disease or condition from occurring in a subject which may be predisposed to the disease or condition but has not yet been diagnosed as having it; (b) inhibiting the disease or condition (e.g., arresting its development); or (c) relieving the disease or condition (e.g., causing regression of the disease or condition, providing improvement in one or more symptoms). Improvements in any conditions can be readily assessed according to standard methods and techniques known in the art. The population of subjects treated by the method of the disease includes subjects suffering from the undesirable condition or disease, as well as subjects at risk for development of the condition or disease.

The term "effective amount" means a dose that produces the desired effect for which it is administered. The exact dose will depend on the purpose of the treatment, and will be ascertainable by one skilled in the art using known techniques. See Lloyd, *The Art, Science and Technology of Pharmaceutical Compounding* (1999).

6.4.1. Routes of Administration

In various embodiments, lasofoxifene is administered by oral, intravenous, transdermal, vaginal topical, or vaginal ring administration.

In some embodiments, lasofoxifene is administered to the patient by oral administration. In certain embodiments, lasofoxifene is administered at about 0.5 mg/day per os to about 10 mg/day per os, such as about 0.5 mg/day per os to about 5 mg/day per os, about 0.5 mg/day per os to about 5 mg/day per os, about 1 mg/day per os to about 5 mg/day per os, about 2 mg/day per os to about 5 mg/day per os, about 3 mg/day per os to about 5 mg/day per os, about 4 mg/day per os to about 5 mg/day per os, about 0.5 mg/day per os to about 4 mg/day per os, about 1 mg/day per os to about 4 mg/day per os, about 2 mg/day per os to about 4 mg/day per os, about 3 mg/day per os to about 4 mg/day per os, about 0.5 mg/day per os to about 3 mg/day per os, about 1 mg/day per os to about 3 mg/day per os, about 2 mg/day per os to about 3 mg/day per os, about 3 mg/day per os, about 0.5 mg/day per os to about 2 mg/day per os, about 1 mg/day per os to about 2 mg/day per os, or about 0.5 mg/day per os to about 1 mg/day per os. In some embodiments, lasofoxifene is administered at about 0.5 mg/day per os. In some embodiments, lasofoxifene is administered at about 1 mg/day per os. In some embodiments, lasofoxifene is administered at about 1.5 mg/day per os. In some embodiments, lasofoxifene is administered at about 2 mg/day per os. In some embodiments, lasofoxifene is administered at about 2.5 mg/day per os. In some embodiments, lasofoxifene is administered at about 3 mg/day per os. In some embodiments, lasofoxifene is administered at about 3.5 mg/day per os. In some embodiments, lasofoxifene is administered at about 4 mg/day per os. In some embodiments, lasofoxifene is administered at about 4.5 mg/day per os. In some embodiments, lasofoxifene is administered at about 5 mg/day per os. In some embodiments, lasofoxifene is administered at about 6 mg/day per os. In some embodiments, lasofoxifene is administered at about 7 mg/day per os. In some embodiments, lasofoxifene is administered at about 8 mg/day per os. In some embodiments, lasofoxifene is administered at about 9 mg/day per os. In some embodiments, lasofoxifene is administered at about 10 mg/day per os. In some other embodiments, lasofoxifene is administered at more than 10 mg/day per os.

In certain embodiments, when lasofoxifene is administered to patient whose cancer has not acquired endocrine resistance, lasofoxifene can be administered at less than 0.5 mg/day per os for prevention of endocrine resistance. In certain embodiments, when lasofoxifene is administered to cancer patient as adjuvant treatment, lasofoxifene can be administered at less than 0.5 mg/day per os for prevention of endocrine resistance.

In certain embodiments, lasofoxifene is administered once every day. In certain embodiments, lasofoxifene is administered once every two days. In certain embodiments, lasofoxifene is administered once every three days. In certain embodiments, lasofoxifene is administered once every four days. In certain embodiments, lasofoxifene is administered once every five days. In certain embodiments, lasofoxifene is administered once every six days. In certain embodiments, lasofoxifene is administered once every week. In certain embodiments, lasofoxifene is administered once every two weeks. In certain embodiments, lasofoxifene is administered once every three weeks. In certain embodiments, lasofoxifene is administered once every month.

In some embodiments, lasofoxifene is administered to the patient by vaginal ring administration. In some of these embodiments, lasofoxifene is administered once every two weeks. In some of these embodiments, lasofoxifene is administered once every three weeks. In some of these embodiments, lasofoxifene is administered once every month. In some of these embodiments, lasofoxifene is administered once every two months. In some of these embodiments, lasofoxifene is administered once every three months. In some of these embodiments, lasofoxifene is administered once every four months.

In some embodiments, lasofoxifene is administered to $ER^+$ cancer patient for one year. In some embodiments, lasofoxifene is administered to the patient for two years. In some embodiments, lasofoxifene is administered to the patient for three years. In some embodiments, lasofoxifene is administered to the patient for four years. In some embodiments, lasofoxifene is administered to the patient for five years. In some other embodiments, lasofoxifene is administered to the patient for more than five years. In certain embodiments, lasofoxifene is administered to the patient until the patient's cancer progresses on therapy.

6.4.2. Combination Therapy

In various embodiments, lasofoxifene is administered either alone or in combination with other therapies. In certain embodiments, lasofoxifene is administered in combination with at least one other therapy. In some embodiments, lasofoxifene and other therapies are administered together (simultaneously). In some other embodiments, lasofoxifene and other therapies are administered at different times (sequentially).

In particular embodiments, the additional therapy that the patient is treated with is endocrine therapy. In various embodiments, the patient is treated with at least one line of additional endocrine therapy. In some embodiments, the patient is treated with one line of additional endocrine therapy. In some other embodiments, the patient is treated with multiple lines of additional endocrine therapy.

In some embodiments, the patient is treated with the additional endocrine therapy at the original doses. In some other embodiments, the patient is treated with the additional endocrine therapy at doses higher than original doses. In certain embodiments, the patient is treated with the additional endocrine therapy at doses lower than original doses.

In certain embodiments, the additional endocrine therapy is treatment with a selective ER modulator (SERM) other than lasofoxifene. In some of these embodiments, the selective ER modulator is selected from tamoxifen, raloxifene, bazedoxifene, toremifene, and ospermifene. In certain embodiments, the selective ER modulator is tamoxifen.

In certain embodiments, the additional endocrine therapy is treatment with a selective ER degrader (SERD). In some of these embodiments, the selective ER degrader is selected from fulvestrant, RAD1901, ARN-810 (GDC-0810), and AZD9496. In certain embodiments, the selective ER degrader is fulvestrant.

In certain embodiments, the additional endocrine therapy is treatment with an aromatase inhibitor. In some of these embodiments, the aromatase inhibitor is selected from exemestane (Aromasin®), letrozole (Femara®), and anastrozole (Arimidex®).

In various embodiments, the additional therapy is administration to the patient of an effective amount of a cell cycle inhibitor. In certain embodiments, the additional therapy is administration of an effective amount of cyclin-dependent kinase 4/6 (CDK4/6) inhibitor. In some embodiments, the additional therapy is a CDK4/6 inhibitor selected from the group of palbociclib, abemaciclib, and ribociclib.

In some embodiments, the additional therapy is administration to the patient of an inhibitor of a pathway that cross-talks with and activates the ER transcriptional activity. In certain embodiments, the additional therapy is a mammalian target of rapamycin (mTOR) inhibitor. In specific embodiments, the mTOR inhibitor is Everolimus. In some of these embodiments, lasofoxifene in combination with Everolimus is administered to a postmenopausal woman with locally advanced or metastatic breast cancer who has progressed on a non-steroidal AI and/or fulvestrant either as monotherapy or in combination with a CDK4/6 inhibitor. In various embodiments, the additional therapy is a phosphoinositide 3-kinase (PI3K) inhibitor or a heat shock protein 90 (HSP90) inhibitor.

In various embodiments, the additional therapy is administration to the patient of an effective amount of a growth factor inhibitor. In certain embodiments, the additional therapy is a human epidermal growth factor receptor 2 (HER2) inhibitor. In some embodiments, the HER2 inhibitor is trastuzumab (Herceptin®). In some other embodiments, the HER2 inhibitor is ado-trastuzumab emtansine (Kadcyla®).

In some embodiments, the additional therapy is administering to the patient an effective amount of a histone deacetylase (HDAC) inhibitor. In various embodiments, the HDAC inhibitor is vorinostat (Zolinza®), romidepsin (Istodax®), chidamide (Epidaza®), panobinostat (Farydak®), belinostat (Beleodaq®, PXD101), valproic acid (Depakote®, Depakene®, Stavzor®), mocetinostat (MGCD0103), abexinostat (PCI-24781), entinostat (MS-275), pracinostat (SB939), resminostat (4SC-201), givinostat (ITF2357), quisinostat (JNJ-26481585), kevetrin, CUDC-101, AR-42, tefinostat (CHR-2835), CHR-3996, 4SC202, CG200745, rocilinostat (ACY-1215), or sulforaphane. In certain embodiments, the HDAC inhibitor is entinostat (MS-275) with the proviso that the patient is not treated with a HER2 inhibitor. In certain other embodiments, the HDAC inhibitor is vorinostat (Zolinza®). In yet certain other embodiments, the HDAC inhibitor is romidepsin (Istodax®).

In some embodiments, the additional therapy is administering to the patient an effective amount of a checkpoint inhibitor. In certain embodiments, the checkpoint inhibitor is an antibody. In some of these embodiments, the checkpoint inhibitor is an antibody specific for programmed cell death protein 1 (PD-1), programmed death-ligand 1 (PD-L1), or cytotoxic T-lymphocyte-associated protein 4 (CTLA-4). In some embodiments, the PD-1 antibody is pembrolizumab (Keytruda®) or nivolumab (Opdivo®). In some embodiments, the CTLA-4 antibody is ipilimumab (Yervoy®).

In certain embodiments, the additional therapy is administering to the patient an effective amount of cancer vaccine.

In some embodiments, the additional therapy is administering to the patient an effective amount of denosumab.

In some embodiments, the additional therapy is administering to the patient an effective amount of a serotonin-norepinephrine reuptake inhibitor (SNRI), a selective serotonin reuptake inhibitor (SSRI), or gabapentin. In certain embodiments, the SNRI is venlafaxine (Effexor®).

6.4.3. Clinical Endpoints 6.4.3.1. Primary Clinical Endpoints

In various embodiments, the method comprises administering an amount of lasofoxifene effective to increase the disease-free survival of the $ER^+$ cancer patient. In some embodiments, the method comprises administering lasofoxifene in an amount effective to reduce recurrence of $ER^+$ cancer. In some embodiments, the method comprises administering lasofoxifene in an amount effective to increase time to recurrence of $ER^+$ cancer. In some embodiments, the method comprises administering lasofoxifene in an amount effective to reduce metastasis of $ER^+$ cancer. In some embodiments, the method comprises administering lasofoxifene in an amount effective to increase duration of progression-free survival of the $ER^+$ cancer patient.

In various embodiments, the method increases the disease-free survival of the $ER^+$ breast cancer patient. In certain embodiments, the method reduces recurrence of $ER^+$ breast cancer. In certain embodiments, the method increases time to recurrence of $ER^+$ breast cancer. In certain embodiments, the method reduces metastasis of $ER^+$ breast cancer to bone. In certain embodiments, the method reduces metastasis of $ER^+$ breast cancer to tissues other than bone. In certain embodiments, the method increases duration of progression-free survival of the $ER^+$ breast cancer patient.

In various embodiments, the method increases the disease-free survival in $ER^+$ cancer patient with endocrine resistance. In some embodiments, the method reduces recurrence of cancer in patient with endocrine resistance. In some embodiments, the method increases time to recurrence of cancer in patient with endocrine resistance. In some embodiments, the method reduces metastasis of cancer in patient with endocrine resistance. In some embodiments, the method increases duration of progression-free survival in $ER^+$ cancer patient with endocrine resistance.

In some preferred embodiments, the method increases disease-free survival, reduces recurrence, increases time to recurrence, reduces metastasis, and/or increases duration of progression-free survival in patients with $ER^+$ locally advanced or metastatic breast cancer that has developed endocrine resistance. In particular embodiments, the breast cancer has developed endocrine resistance by acquiring one or more of the ESR1 mutations discussed herein. In some embodiments, the method reduces the selective pressure and prevents the expansion of the endocrine resistant clones in $ER^+$ locally advanced or metastatic breast cancer during treatment.

6.4.3.2. Secondary Clinical Endpoints

In some embodiments, the method is effective to prevent fracture and bone loss in women who are concurrently being treated with one or more drugs causing or predisposing to osteoporosis.

In some embodiments, the method is effective to decrease vaginal pH, increase vaginal lubrication, and/or improve vaginal cell maturation index in women who are concurrently being treated with one or more drugs causing or predisposing to vulvovaginal atrophy (VVA).

In some embodiments, the method reduces one or more symptoms of sexual dysfunction in women who are concurrently being treated with one or more drugs causing or predisposing to sexual dysfunction.

In some embodiments, the method treats hot flashes in women who are concurrently being treated with one or more drugs causing or predisposing to hot flashes.

In some embodiments, the method increases one or more quality of life measures selected from joint ache, urogenital symptoms, bone loss, and bone fractures.

6.5. Further Embodiments

Further embodiments are provided in the following numbered embodiments.

1. A method of treating locally advanced or metastatic breast cancer in women, comprising:
   a) selecting for treatment a patient who has been diagnosed with estrogen receptor positive (ER+) locally advanced or metastatic breast cancer; and
   b) administering to the selected patient an effective amount of lasofoxifene, a pharmaceutically acceptable salt thereof, or a prodrug thereof.
2. The method of embodiment 1, wherein the patient has previously been treated with one or more lines of endocrine therapy.
3. The method of embodiment 2, wherein the patient has previously been treated with a plurality of lines of endocrine therapy.
4. The method of embodiment 2 or embodiment 3, wherein the endocrine therapy that the patient has previously been treated with is a selective ER modulator (SERM).
5. The method of embodiment 4, wherein the SERM is tamoxifen, raloxifene, bazedoxifene, toremifene, or ospemifene.
6. The method of embodiment 2 or embodiment 3, wherein the endocrine therapy that the patient has previously been treated with is a selective ER degrader (SERD).
7. The method of embodiment 6, wherein the SERD is fulvestrant, RAD1901, ARN-810 (GDC-0810), or AZD9496.
8. The method of embodiment 2 or embodiment 3, wherein the endocrine therapy that the patient has previously been treated with is an aromatase inhibitor.
9. The method of embodiment 8, wherein the aromatase inhibitor is exemestane (Aromasin®), letrozole (Femara®), or anastrozole (Arimidex®).
10. The method of any one of embodiments 2 to 9, wherein the patient has disease progression after endocrine therapy.
11. The method of any one of embodiments 1 to 10, wherein the patient's locally advanced or metastatic cancer is resistant to endocrine therapy other than lasofoxifene.
12. The method of any one of embodiments 1 to 11, wherein the patient's locally advanced or metastatic cancer has at least one gain of function missense mutation within the ligand binding domain (LBD) of the Estrogen Receptor 1 (ESR1) gene.
13. The method of embodiment 12, wherein the patient has previously been determined to have at least one gain of function missense mutation within the ligand binding domain (LBD) of the Estrogen Receptor 1 (ESR1) gene.
14. The method of embodiment 13, further comprising the earlier step of:
   determining that the patient has at least one gain of function missense mutation within the ligand binding domain (LBD) of the Estrogen Receptor 1 (ESR1) gene.
15. The method of any one of embodiments 12 to 14, wherein the at least one of gain of function missense mutation is in any one of amino acids D538, Y537, L536, P535, V534, S463, V392, and E380.
16. The method of embodiment 15, wherein the at least one gain of function missense mutation is in the amino acid D538.
17. The method of embodiment 16, wherein the mutation is D538G.
18. The method of embodiment 15, wherein the at least one gain of function missense mutation is in the amino acid Y537.
19. The method of embodiment 18, wherein the mutation is Y537S, Y537N, Y537C, or Y537Q.
20. The method of embodiment 19, wherein the mutation is Y537C.
21. The method of embodiment 15, wherein the at least one gain of function missense mutation is in the amino acid L536.
22. The method of embodiment 21, wherein the mutation is L536R or L536Q.
23. The method of embodiment 15, wherein the at least one gain of function missense mutation is in the amino acid P535.
24. The method of embodiment 23, wherein the mutation is P535H.
25. The method of embodiment 15, wherein the at least one gain of function missense mutation is in the amino acid V534.
26. The method of embodiment 25, wherein the mutation is V534E.
27. The method of embodiment 15, wherein the at least one gain of function missense mutation is in the amino acid S463.
28. The method of embodiment 27, wherein the mutation is S463P.
29. The method of embodiment 15, wherein the at least one gain of function missense mutation is in the amino acid V392.
30. The method of embodiment 29, wherein the mutation is V392I.
31. The method of embodiment 15, wherein the at least one gain of function missense mutation is in the amino acid E380.
32. The method of embodiment 31, wherein the mutation is E380Q.
33. The method of any one of embodiments 12 to 32, wherein the serum estradiol level of the patient is at least 0.35 ng/dL.
34. The method of any one of embodiments 12 to 32, wherein the serum estradiol level of the patient is about 0.30 ng/dL to about 0.35 ng/dL.
35. The method of any one of embodiments 12 to 32, wherein the serum estradiol level of the patient is about 0.25 ng/dL to about 0.30 ng/dL.
36. The method of any one of embodiments 1 to 35, wherein lasofoxifene is administered as lasofoxifene tartrate.

37. The method of any one of embodiments 1 to 36, wherein lasofoxifene is administered by oral, intravenous, transdermal, vaginal topical, or vaginal ring administration.

38. The method of embodiment 37, wherein lasofoxifene is administered by oral administration.

39. The method of embodiment 38, wherein lasofoxifene is administered at about 0.5 mg/day per os to about 10 mg/day per os.

40. The method of embodiment 39, wherein lasofoxifene is administered at about 0.5 mg/day per os to about 5 mg/day per os.

41. The method of embodiment 40, wherein lasofoxifene is administered at about 1 mg/day per os to about 5 mg/day per os.

42. The method of embodiment 40, wherein lasofoxifene is administered at 1 mg/day per os.

43. The method of embodiment 40, wherein lasofoxifene is administered at 5 mg/day per os.

44. The method of any one of embodiments 1 to 43, wherein lasofoxifene is administered once every day, once every two days, once every three days, once every four days, once every five days, once every six days, once every week, once every two weeks, once every three weeks, or once every month.

45. The method of any one of embodiments 1 to 44, further comprising treating said patient with at least one additional endocrine therapy.

46. The method of embodiment 45, wherein said patient is treated with the additional endocrine therapy at original doses.

47. The method of embodiment 45, wherein said patient is treated with the additional endocrine therapy at doses higher than original doses.

48. The method of any one of embodiments 45 to 47, wherein the additional endocrine therapy is treatment with a selective ER modulator (SERM) other than lasofoxifene.

49. The method of any one of embodiments 45 to 47, wherein the additional endocrine therapy is treatment with a selective ER degrader (SERD).

50. The method of any one of embodiments 45 to 47, wherein the additional endocrine therapy is treatment with an aromatase inhibitor.

51. The method of any one of embodiments 1 to 44, further comprising administering to said patient an effective amount of cyclin-dependent kinase 4/6 (CDK4/6) inhibitor.

52. The method of embodiment 51, wherein said CDK4/6 inhibitor is palbociclib, abemaciclib, or ribociclib.

53. The method of any one of embodiments 1 to 44, further comprising administering to said patient an effective amount of mammalian target of rapamycin (mTOR) inhibitor.

54. The method of embodiment 53, wherein said mTOR inhibitor is Everolimus.

55. The method of any one of embodiments 1 to 44, further comprising administering to said patient an effective amount of phosphoinositide 3-kinase (PI3K) inhibitor or heat shock protein 90 (HSP90) inhibitor.

56. The method of any one of embodiments 1 to 44, further comprising administering to said patient an effective amount of human epidermal growth factor receptor 2 (HER2) inhibitor.

57. The method of embodiment 56, wherein said HER2 inhibitor is trastuzumab (Herceptin®) or ado-trastuzumab emtansine (Kadcyla®).

58. The method of any one of embodiments 1 to 44, further comprising administering to said patient an effective amount of a histone deacetylase (HDAC) inhibitor.

59. The method of embodiment 58, wherein said HDAC inhibitor is vorinostat (Zolinza®), romidepsin (Istodax®), chidamide (Epidaza®), panobinostat (Farydak®), belinostat (Beleodaq®, PXD101), valproic acid (Depakote®, Depakene®, Stavzor®), mocetinostat (MGCD0103), abexinostat (PCI-24781), entinostat (MS-275), pracinostat (SB939), resminostat (4SC-201), givinostat (ITF2357), quisinostat (JNJ-26481585), kevetrin, CUDC-101, AR-42, tefinostat (CHR-2835), CHR-3996, 4SC202, CG200745, rocilinostat (ACY-1215), or sulforaphane.

60. The method of any one of embodiments 1 to 44, further comprising administering to said patient an effective amount of a checkpoint inhibitor.

61. The method of embodiment 60, wherein said checkpoint inhibitor is an antibody specific for programmed cell death protein 1 (PD-1), programmed death-ligand 1 (PD-L1), or cytotoxic T-lymphocyte-associated protein 4 (CTLA-4).

62. The method of embodiment 61, wherein said PD-1 antibody is pembrolizumab (Keytruda®) or nivolumab (Opdivo®).

63. The method of embodiment 61, wherein said CTLA-4 antibody is ipilimumab (Yervoy®).

64. The method of any one of embodiments 1 to 44, further comprising administering to said patient an effective amount of cancer vaccine.

65. The method of any one of embodiments 1 to 64, wherein the patient is premenopausal.

66. The method of embodiment 65, wherein the patient has locally advanced or metastatic ER+/HER2− breast cancer.

67. The method of embodiment 65, wherein the patient has progressed on her first hormonal treatment while on a non-steroid aromatase inhibitor (AI), fulvestrant, AI in combination with a CDK4/6 inhibitor, or fulvestrant in combination with a CDK4/6 inhibitor.

68. The method of any one of embodiments 1 to 64, wherein the patient is perimenopausal.

69. The method of embodiment 68, wherein the patient has locally advanced or metastatic ER+/HER2− breast cancer.

70. The method of embodiment 69, wherein the patient has progressed on her first hormonal treatment while on a non-steroid aromatase inhibitor (AI), fulvestrant, AI in combination with a CDK4/6 inhibitor, or fulvestrant in combination with a CDK4/6 inhibitor.

71. The method of any one of embodiments 1 to 64, wherein the patient is postmenopausal.

72. The method of embodiment 71, wherein the patient has locally advanced or metastatic ER+/HER2− breast cancer.

73. The method of embodiment 72, wherein the patient has progressed on her first hormonal treatment while on a non-steroid aromatase inhibitor (AI), fulvestrant, AI in combination with a CDK4/6 inhibitor, or fulvestrant in combination with a CDK4/6 inhibitor.

74. A method of treating primary breast cancer in women, comprising:
   a) selecting for treatment a patient who has been diagnosed with estrogen receptor positive (ER+) primary breast cancer; and
   b) administering to the selected patient an effective amount of lasofoxifene, a pharmaceutically acceptable salt thereof, or a prodrug thereof.

75. The method of embodiment 74, wherein lasofoxifene is administered as lasofoxifene tartrate.

76. The method of embodiment 74 or embodiment 75, wherein lasofoxifene is administered by oral, intravenous, transdermal, vaginal topical, or vaginal ring administration.

77. The method of embodiment 76, wherein lasofoxifene is administered by oral administration.

78. The method of embodiment 77, wherein lasofoxifene is administered at about 0.5 mg/day per os to about 10 mg/day per os.
79. The method of embodiment 78, wherein lasofoxifene is administered at about 0.5 mg/day per os to about 5 mg/day per os.
80. The method of embodiment 79, wherein lasofoxifene is administered at about 1 mg/day per os to about 5 mg/day per os.
81. The method of embodiment 79, wherein lasofoxifene is administered at 1 mg/day per os.
82. The method of embodiment 79, wherein lasofoxifene is administered at 5 mg/day per os.
83. The method of any one of embodiments 74 to 82, wherein lasofoxifene is administered once every day, once every two days, once every three days, once every four days, once every five days, once every six days, once every week, once every two weeks, once every three weeks, or once every month.
84. The method of any one of embodiments 74 to 83, further comprising treating said patient with at least one additional endocrine therapy.
85. The method of embodiment 84, wherein said patient is treated with the additional endocrine therapy at original doses.
86. The method of embodiment 84, wherein said patient is treated with the additional endocrine therapy at doses higher than original doses.
87. The method of any one of embodiments 84 to 86, wherein the additional endocrine therapy is treatment with a selective ER modulator (SERM) other than lasofoxifene.
88. The method of any one of embodiments 84 to 86, wherein the additional endocrine therapy is treatment with a selective ER degrader (SERD).
89. The method of any one of embodiments 84 to 86, wherein the additional endocrine therapy is treatment with an aromatase inhibitor.
90. The method of any one of embodiments 74 to 83, further comprising administering to said patient an effective amount of cyclin-dependent kinase 4/6 (CDK4/6) inhibitor.
91. The method of embodiment 90, wherein said CDK4/6 inhibitor is palbociclib, abemaciclib, or ribociclib.
92. The method of any one of embodiments 74 to 83, further comprising administering to said patient an effective amount of mammalian target of rapamycin (mTOR) inhibitor.
93. The method of embodiment 92, wherein said mTOR inhibitor is Everolimus.
94. The method of any one of embodiments 74 to 83, further comprising administering to said patient an effective amount of phosphoinositide 3-kinase (PI3K) inhibitor or heat shock protein 90 (HSP90) inhibitor.
95. The method of any one of embodiments 74 to 83, further comprising administering to said patient an effective amount of human epidermal growth factor receptor 2 (HER2) inhibitor.
96. The method of embodiment 95, wherein said HER2 inhibitor is trastuzumab (Herceptin®) or ado-trastuzumab emtansine (Kadcyla®).
97. The method of any one of embodiments 74 to 83, further comprising administering to said patient an effective amount of a histone deacetylase (HDAC) inhibitor.
98. The method of embodiment 97, wherein said HDAC inhibitor is vorinostat (Zolinza®), romidepsin (Istodax®), chidamide (Epidaza®), panobinostat (Farydak®), belinostat (Beleodaq®, PXD101), valproic acid (Depakote®, Depakene®, Stavzor®), mocetinostat (MGCD0103), abexinostat (PCI-24781), entinostat (MS-275), pracinostat (SB939), resminostat (4SC-201), givinostat (ITF2357), quisinostat (JNJ-26481585), kevetrin, CUDC-101, AR-42, tefinostat (CHR-2835), CHR-3996, 4SC202, CG200745, rocilinostat (ACY-1215), or sulforaphane.
99. The method of any one of embodiments 74 to 83, further comprising administering to said patient an effective amount of checkpoint inhibitor.
100. The method of embodiment 99, wherein said checkpoint inhibitor is an antibody specific for programmed cell death protein 1 (PD-1), programmed death-ligand 1 (PD-L1), or cytotoxic T-lymphocyte-associated protein 4 (CTLA-4).
101. The method of embodiment 100, wherein said PD-1 antibody is pembrolizumab (Keytruda®) or nivolumab (Opdivo®).
102. The method of embodiment 100, wherein said CTLA-4 antibody is ipilimumab (Yervoy®).
103. The method of any one of embodiments 74 to 83, further comprising administering to said patient an effective amount of cancer vaccine.
104. The method of any one of embodiments 74 to 103, wherein the patient is premenopausal.
105. The method of any one of embodiments 74 to 103, wherein the patient is perimenopausal.
106. The method of any one of embodiments 74 to 103, wherein the patient is postmenopausal.
107. A method of adjuvant therapy of estrogen receptor positive (ER+) breast cancer, comprising:
administering to a patient who has received primary treatment for ER+ breast cancer an effective amount of lasofoxifene, a pharmaceutically acceptable salt thereof, or a prodrug thereof, in combination with an aromatase inhibitor.
108. The method of embodiment 107, wherein lasofoxifene is administered continuously during the administration of the aromatase inhibitor.
109. The method of embodiment 107, wherein lasofoxifene is administered cyclically during the administration of the aromatase inhibitor.
110. The method of any one of embodiments 107 to 109, wherein the dosing regimen of lasofoxifene is different from the dosing regimen of the aromatase inhibitor.
111. The method of any one of embodiments 107 to 110, wherein lasofoxifene is administered as lasofoxifene tartrate.
112. The method of any one of embodiments 107 to 111, wherein the aromatase inhibitor is exemestane (Aromasin®), letrozole (Femara®), or anastrozole (Arimidex®).
113. The method of any one of embodiments 107 to 112, wherein lasofoxifene is administered by oral, intravenous, transdermal, vaginal topical, or vaginal ring administration.
114. The method of embodiment 113, wherein lasofoxifene is administered by oral administration.
115. The method of embodiment 114, wherein lasofoxifene is administered at about 0.5 mg/day per os to about 10 mg/day per os.
116. The method of embodiment 115, wherein lasofoxifene is administered at about 0.5 mg/day per os to about 5 mg/day per os.
117. The method of embodiment 116, wherein lasofoxifene is administered at about 1 mg/day per os to about 5 mg/day per os.
118. The method of embodiment 116, wherein lasofoxifene is administered at 1 mg/day per os.
119. The method of embodiment 116, wherein lasofoxifene is administered at 5 mg/day per os.

120. The method of any one of embodiments 107 to 119, wherein lasofoxifene is administered once every day, once every two days, once every three days, once every four days, once every five days, once every six days, once every week, once every two weeks, once every three weeks, or once every month.

121. The method of any one of embodiments 107 to 120, further comprising treating said patient with an additional endocrine therapy.

122. The method of embodiment 121, wherein the additional endocrine therapy is treatment with a selective ER degrader (SERD).

123. The method of any one of embodiments 107 to 120, further comprising administering to said patient an effective amount of cyclin-dependent kinase 4/6 (CDK4/6) inhibitor.

124. The method of embodiment 123, wherein said CDK4/6 inhibitor is palbociclib, abemaciclib, or ribociclib.

125. The method of any one of embodiments 107 to 120, further comprising administering to said patient an effective amount of mammalian target of rapamycin (mTOR) inhibitor.

126. The method of embodiment 125, wherein said mTOR inhibitor is Everolimus.

127. The method of any one of embodiments 107 to 120, further comprising administering to said patient an effective amount of phosphoinositide 3-kinase (PI3K) inhibitor or heat shock protein 90 (HSP90) inhibitor.

128. The method of any one of embodiments 107 to 120, further comprising administering to said patient an effective amount of human epidermal growth factor receptor 2 (HER2) inhibitor.

129. The method of embodiment 128, wherein said HER2 inhibitor is trastuzumab (Herceptin®) or ado-trastuzumab emtansine (Kadcyla®).

130. The method of any one of embodiments 107 to 120, further comprising administering to said patient an effective amount of a histone deacetylase (HDAC) inhibitor.

131. The method of embodiment 130, wherein said HDAC inhibitor is vorinostat (Zolinza®), romidepsin (Istodax®), chidamide (Epidaza®), panobinostat (Farydak®), belinostat (Beleodaq®, PXD101), valproic acid (Depakote®, Depakene®, Stavzor®), mocetinostat (MGCD0103), abexinostat (PCI-24781), entinostat (MS-275), pracinostat (SB939), resminostat (4SC-201), givinostat (ITF2357), quisinostat (JNJ-26481585), kevetrin, CUDC-101, AR-42, tefinostat (CHR-2835), CHR-3996, 4SC202, CG200745, rocilinostat (ACY-1215), or sulforaphane.

132. The method of any one of embodiments 107 to 120, further comprising administering to said patient an effective amount of checkpoint inhibitor.

133. The method of embodiment 132, wherein said checkpoint inhibitor is an antibody specific for programmed cell death protein 1 (PD-1), programmed death-ligand 1 (PD-L1), or cytotoxic T-lymphocyte-associated protein 4 (CTLA-4).

134. The method of embodiment 133, wherein said PD-1 antibody is pembrolizumab (Keytruda®) or nivolumab (Opdivo®).

135. The method of embodiment 133, wherein said CTLA-4 antibody is ipilimumab (Yervoy®).

136. The method of any one of embodiments 107 to 120, further comprising administering to said patient an effective amount of cancer vaccine.

137. The method of any one of embodiments 107 to 136, wherein lasofoxifene is administered in an amount and on a schedule sufficient to improve bone mass.

138. The method of any one of embodiments 107 to 136, wherein lasofoxifene is administered in an amount and on a schedule sufficient to improve symptoms of VVA.

139. The method of any one of embodiments 107 to 138, wherein the patient is premenopausal.

140. The method of any one of embodiments 107 to 138, wherein the patient is perimenopausal.

141. The method of any one of embodiments 107 to 138, wherein the patient is postmenopausal.

142. A method of treating cancers other than breast cancer in women, comprising:
  a) selecting for treatment a patient who has been diagnosed with estrogen receptor positive (ER+) cancer, other than breast cancer, and has at least one gain of function mutations in the Estrogen Receptor 1 (ESR1) gene; and
  b) administering to the selected patient an effective amount of lasofoxifene, a pharmaceutically acceptable salt thereof, or a prodrug thereof.

143. The method of embodiment 142, wherein the patient has been diagnosed with ER+ ovarian cancer.

144. The method of embodiment 142, wherein the patient has been diagnosed with ER+ lung cancer.

145. The method of any one of embodiments 142 to 144, wherein lasofoxifene is administered as lasofoxifene tartrate.

146. The method of any one of embodiments 142 to 145, wherein lasofoxifene is administered by oral, intravenous, transdermal, vaginal topical, or vaginal ring administration.

147. The method of embodiment 146, wherein lasofoxifene is administered by oral administration.

148. The method of embodiment 147, wherein lasofoxifene is administered at about 0.5 mg/day per os to about 10 mg/day per os.

149. The method of embodiment 148, wherein lasofoxifene is administered at about 0.5 mg/day per os to about 5 mg/day per os.

150. The method of embodiment 149, wherein lasofoxifene is administered at about 1 mg/day per os to about 5 mg/day per os.

151. The method of embodiment 149, wherein lasofoxifene is administered at 1 mg/day per os.

152. The method of embodiment 149, wherein lasofoxifene is administered at 5 mg/day per os.

153. The method of any one of embodiments 142 to 152, wherein lasofoxifene is administered once every day, once every two days, once every three days, once every four days, once every five days, once every six days, once every week, once every two weeks, once every three weeks, or once every month.

154. The method of any one of embodiments 142 to 153, further comprising treating said patient with at least one additional endocrine therapy.

155. The method of embodiment 154, wherein said patient is treated with the additional endocrine therapy at original doses.

156. The method of embodiment 154, wherein said patient is treated with the additional endocrine therapy at doses higher than original doses.

157. The method of any one of embodiments 154 to 156, wherein the additional endocrine therapy is treatment with a selective ER modulator (SERM) other than lasofoxifene.

158. The method of any one of embodiments 154 to 156, wherein the additional endocrine therapy is treatment with a selective ER degrader (SERD).

159. The method of any one of embodiments 154 to 156, wherein the additional endocrine therapy is treatment with an aromatase inhibitor.

160. The method of any one of embodiments 142 to 153, further comprising administering to said patient an effective amount of cyclin-dependent kinase 4/6 (CDK4/6) inhibitor.
161. The method of embodiment 160, wherein said CDK4/6 inhibitor is palbociclib, abemaciclib, or ribociclib.
162. The method of any one of embodiments 142 to 153, further comprising administering to said patient an effective amount of mammalian target of rapamycin (mTOR) inhibitor.
163. The method of embodiment 162, wherein said mTOR inhibitor is Everolimus.
164. The method of any one of embodiments 142 to 153, further comprising administering to said patient an effective amount of phosphoinositide 3-kinase (PI3K) inhibitor or heat shock protein 90 (HSP90) inhibitor.
165. The method of any one of embodiments 142 to 153, further comprising administering to said patient an effective amount of human epidermal growth factor receptor 2 (HER2) inhibitor.
166. The method of embodiment 165, wherein said HER2 inhibitor is trastuzumab (Herceptin®) or ado-trastuzumab emtansine (Kadcyla®).
167. The method of any one of embodiments 142 to 153, further comprising administering to said patient an effective amount of a histone deacetylase (HDAC) inhibitor.
168. The method of embodiment 167, wherein said HDAC inhibitor is vorinostat (Zolinza®), romidepsin (Istodax®), chidamide (Epidaza®), panobinostat (Farydak®), belinostat (Beleodaq®, PXD101), valproic acid (Depakote®, Depakene®, Stavzor®), mocetinostat (MGCD0103), abexinostat (PCI-24781), entinostat (MS-275), pracinostat (SB939), resminostat (4SC-201), givinostat (ITF2357), quisinostat (JNJ-26481585), kevetrin, CUDC-101, AR-42, tefinostat (CHR-2835), CHR-3996, 4SC202, CG200745, rocilinostat (ACY-1215), or sulforaphane.
169. The method of any one of embodiments 142 to 153, further comprising administering to said patient an effective amount of checkpoint inhibitor.
170. The method of embodiment 169, wherein said checkpoint inhibitor is an antibody specific for programmed cell death protein 1 (PD-1), programmed death-ligand 1 (PD-L1), or cytotoxic T-lymphocyte-associated protein 4 (CTLA-4).
171. The method of embodiment 170, wherein said PD-1 antibody is pembrolizumab (Keytruda®) or nivolumab (Opdivo®).
172. The method of embodiment 170, wherein said CTLA-4 antibody is ipilimumab (Yervoy®).
173. The method of any one of embodiments 142 to 153, further comprising administering to said patient an effective amount of cancer vaccine.
174. The method of any one of embodiments 142 to 173, wherein the patient is premenopausal.
175. The method of any one of embodiments 142 to 173, wherein the patient is perimenopausal.
176. The method of any one of embodiments 142 to 173, wherein the patient is postmenopausal.
177. A method of treating a female patient suffering from breast cancer who is at risk of acquiring a gain of function missense mutation within the ligand binding domain (LBD) of the Estrogen Receptor 1 (ESR1) gene, comprising administering to the female patient an effective amount of lasofoxifene, a pharmaceutically acceptable salt thereof, or a prodrug thereof.
178. A method of treating a female patient suffering from breast cancer who is at risk of acquiring resistance to endocrine therapy, optionally wherein the endocrine therapy is (i) selective ER modulator (SERM) therapy, (ii) selective ER degrader (SERD) therapy, (iii) aromatase inhibitor (AI) therapy, or (iv) any combination of (i), (ii) and/or (iii), comprising administering to the female patient an effective amount of lasofoxifene, a pharmaceutically acceptable salt thereof, or a prodrug thereof.
179. The method of embodiment 177 or embodiment 178, wherein the patient has primary breast cancer.
180. The method of embodiment 179, wherein the primary breast cancer is locally advanced.
181. The method of any one of embodiments 177 to 180, wherein the patient has been treated with endocrine therapy, optionally wherein the endocrine therapy is (i) selective ER modulator (SERM) therapy, (ii) selective ER degrader (SERD) therapy, (iii) aromatase inhibitor (AI) therapy, or (iv) any combination of (i), (ii) and/or (iii).
182. A method of treating a female patient suffering from estrogen receptor positive (ER+) primary breast cancer, comprising administering to a female patient an effective amount of lasofoxifene, a pharmaceutically acceptable salt thereof, or a prodrug thereof.
183. The method of embodiment 182, wherein the patient is at risk of acquiring resistance to endocrine therapy, optionally wherein the endocrine therapy is (i) selective ER modulator (SERM) therapy, (ii) selective ER degrader (SERD) therapy, (iii) aromatase inhibitor (AI) therapy, or (iv) any combination of (i), (ii) and/or (iii).
184. The method of embodiment 182 or embodiment 183, wherein the primary breast cancer is locally advanced.
185. The method of any one of embodiments 182 to 184, wherein the patient has been treated with endocrine therapy, optionally wherein the endocrine therapy is (i) selective ER modulator (SERM) therapy, (ii) selective ER degrader (SERD) therapy, (iii) aromatase inhibitor (AI) therapy, or (iv) any combination of (i), (ii) and/or (iii).
186. A method of treating a female patient suffering from estrogen receptor positive (ER+) locally advanced or metastatic breast cancer, comprising administering to a female patient an effective amount of lasofoxifene, a pharmaceutically acceptable salt thereof, or a prodrug thereof.
187. The method of embodiment 186, wherein the patient has previously been treated with one or more lines of endocrine therapy.
188. The method of embodiment 186, wherein the patient has previously been treated with a plurality of lines of endocrine therapy.
189. The method of any one of embodiments 186 to 188, wherein the patient has disease progression after endocrine therapy.
190. The method of any one of embodiments 186 to 188, wherein the endocrine therapy that the patient has previously been treated with is a selective ER modulator (SERM).
191. The method of embodiment 190, wherein the SERM is tamoxifen, raloxifene, bazedoxifene, toremifene, or ospemifene.
192. The method any one of embodiments 186 to 188, wherein the endocrine therapy that the patient has previously been treated with is a selective ER degrader (SERD).
193. The method of embodiment 192, wherein the SERD is fulvestrant, RAD1901, ARN-810 (GDC-0810), or AZD9496.
194. The method of any one of embodiments 186 to 188, wherein the endocrine therapy that the patient has previously been treated with is an aromatase inhibitor.
195. The method of embodiment 194, wherein the aromatase inhibitor is exemestane (Aromasin®), letrozole (Femara®), or anastrozole (Arimidex®).

196. The method of any one of embodiments 187 to 195, wherein the patient has disease progression after endocrine therapy.
197. The method of any one of embodiments 186 to 196, wherein the patient's locally advanced or metastatic cancer is resistant to endocrine therapy other than lasofoxifene.
198. The method of any one of embodiments 186 to 197, wherein the patient has cancer cells with at least one gain of function missense mutation within the ligand binding domain (LBD) of the Estrogen Receptor 1 (ESR1) gene.
199. The method of embodiment 198, wherein the patient has previously been determined to have at least one gain of function missense mutation within the ligand binding domain (LBD) of the Estrogen Receptor 1 (ESR1) gene.
200. The method of embodiment 197, further comprising the earlier step of:
  determining that the patient has at least one gain of function missense mutation within the ligand binding domain (LBD) of the Estrogen Receptor 1 (ESR1) gene.
201. The method of any one of embodiments 198 to 198, wherein the at least one of gain of function missense mutation is in any one of amino acids D538, Y537, L536, P535, V534, S463, V392, and E380.
202. The method of embodiment 201, wherein the at least one gain of function missense mutation is in the amino acid D538.
203. The method of embodiment 202, wherein the mutation is D538G.
204. The method of embodiment 201, wherein the at least one gain of function missense mutation is in the amino acid Y537.
205. The method of embodiment 204, wherein the mutation is Y537S, Y537N, Y537C, or Y537Q.
206. The method of embodiment 205, wherein the mutation is Y537C.
207. The method of embodiment 201, wherein the at least one gain of function missense mutation is in the amino acid L536.
208. The method of embodiment 207, wherein the mutation is L536R or L536Q.
209. The method of embodiment 201, wherein the at least one gain of function missense mutation is in the amino acid P535.
210. The method of embodiment 209, wherein the mutation is P535H.
211. The method of embodiment 201, wherein the at least one gain of function missense mutation is in the amino acid V534.
212. The method of embodiment 211, wherein the mutation is V534E.
213. The method of embodiment 201, wherein the at least one gain of function missense mutation is in the amino acid S463.
214. The method of embodiment 213, wherein the mutation is S463P.
215. The method of embodiment 201, wherein the at least one gain of function missense mutation is in the amino acid V392.
216. The method of embodiment 215, wherein the mutation is V392I.
217. The method of embodiment 201, wherein the at least one gain of function missense mutation is in the amino acid E380.
218. The method of embodiment 217, wherein the mutation is E380Q.
219. The method of any one of embodiments 177 to 218, wherein lasofoxifene is administered as lasofoxifene tartrate.
220. The method of any one of embodiments 177 to 219, wherein lasofoxifene is administered by oral, intravenous, transdermal, vaginal topical, or vaginal ring administration.
221. The method of embodiment 220, wherein lasofoxifene is administered by oral administration.
222. The method of embodiment 221, wherein lasofoxifene is administered at about 0.5 mg/day per os to about 10 mg/day per os.
223. The method of embodiment 222, wherein lasofoxifene is administered at about 0.5 mg/day per os to about 5 mg/day per os.
224. The method of embodiment 223, wherein lasofoxifene is administered at about 1 mg/day per os to about 5 mg/day per os.
225. The method of embodiment 223, wherein lasofoxifene is administered at 1 mg/day per os.
226. The method of embodiment 223, wherein lasofoxifene is administered at 5 mg/day per os.
227. The method of any one of embodiments 177 to 226, wherein lasofoxifene is administered once every day, once every two days, once every three days, once every four days, once every five days, once every six days, once every week, once every two weeks, once every three weeks, or once every month.
228. The method of any one of embodiments 177 to 227, further comprising treating said patient with at least one additional endocrine therapy.
229. The method of embodiment 228, wherein said patient is treated with the additional endocrine therapy at original doses.
230. The method of embodiment 228, wherein said patient is treated with the additional endocrine therapy at doses higher than original doses.
231. The method of any one of embodiments 228 to 230, wherein the additional endocrine therapy is treatment with a selective ER modulator (SERM) other than lasofoxifene.
232. The method of any one of embodiments 228 to 230, wherein the additional endocrine therapy is treatment with a selective ER degrader (SERD).
233. The method of any one of embodiments 228 to 230, wherein the additional endocrine therapy is treatment with an aromatase inhibitor.
234. The method of any one of embodiments 177 to 227, further comprising administering to said patient an effective amount of cyclin-dependent kinase 4/6 (CDK4/6) inhibitor.
235. The method of embodiment 234, wherein said CDK4/6 inhibitor is palbociclib, abemaciclib, or ribociclib.
236. The method of any one of embodiments 177 to 227, further comprising administering to said patient an effective amount of mammalian target of rapamycin (mTOR) inhibitor.
237. The method of embodiment 236, wherein said mTOR inhibitor is Everolimus.
238. The method of any one of embodiments 177 to 227, further comprising administering to said patient an effective amount of phosphoinositide 3-kinase (PI3K) inhibitor or heat shock protein 90 (HSP90) inhibitor.
239. The method of any one of embodiments 177 to 227, further comprising administering to said patient an effective amount of human epidermal growth factor receptor 2 (HER2) inhibitor.
240. The method of embodiment 239, wherein said HER2 inhibitor is trastuzumab (Herceptin®) or ado-trastuzumab emtansine (Kadcyla®).

241. The method of any one of embodiments 177 to 227, further comprising administering to said patient an effective amount of a histone deacetylase (HDAC) inhibitor.

242. The method of embodiment 241, wherein said HDAC inhibitor is vorinostat (Zolinza®), romidepsin (Istodax®), chidamide (Epidaza®), panobinostat (Farydak®), belinostat (Beleodaq®, PXD101), valproic acid (Depakote®, Depakene®, Stavzor®), mocetinostat (MGCD0103), abexinostat (PCI-24781), entinostat (MS-275), pracinostat (SB939), resminostat (4SC-201), givinostat (ITF2357), quisinostat (JNJ-26481585), kevetrin, CUDC-101, AR-42, tefinostat (CHR-2835), CHR-3996, 4SC202, CG200745, rocilinostat (ACY-1215), or sulforaphane.

243. The method of any one of embodiments 177 to 227, further comprising administering to said patient an effective amount of a checkpoint inhibitor.

244. The method of embodiment 243, wherein said checkpoint inhibitor is an antibody specific for programmed cell death protein 1 (PD-1), programmed death-ligand 1 (PD-L1), or cytotoxic T-lymphocyte-associated protein 4 (CTLA-4).

245. The method of embodiment 244, wherein said PD-1 antibody is pembrolizumab (Keytruda®) or nivolumab (Opdivo®).

246. The method of embodiment 244, wherein said CTLA-4 antibody is ipilimumab (Yervoy®).

247. The method of any one of embodiments 177 to 227, further comprising administering to said patient an effective amount of cancer vaccine.

248. The method of any one of embodiments 177 to 247, wherein the patient is premenopausal.

249. The method of embodiment 248, wherein the patient has locally advanced or metastatic ER+/HER2− breast cancer.

250. The method of embodiment 249, wherein the patient has progressed on her first hormonal treatment while on a non-steroid aromatase inhibitor (AI), fulvestrant, AI in combination with a CDK4/6 inhibitor, or fulvestrant in combination with a CDK4/6 inhibitor.

251. The method of any one of embodiments 177 to 247, wherein the patient is perimenopausal.

252. The method of embodiment 251, wherein the patient has locally advanced or metastatic ER+/HER2− breast cancer.

253. The method of embodiment 252, wherein the patient has progressed on her first hormonal treatment while on a non-steroid aromatase inhibitor (AI), fulvestrant, AI in combination with a CDK4/6 inhibitor, or fulvestrant in combination with a CDK4/6 inhibitor.

254. The method of any one of embodiments 177 to 247, wherein the patient is postmenopausal.

255. The method of embodiment 254, wherein the patient has locally advanced or metastatic ER+/HER2− breast cancer.

256. The method of embodiment 255, wherein the patient has progressed on her first hormonal treatment while on a non-steroid aromatase inhibitor (AI), fulvestrant, AI in combination with a CDK4/6 inhibitor, or fulvestrant in combination with a CDK4/6 inhibitor.

6.6. Examples

Below are examples of specific embodiments for carrying out the present invention. The examples are offered for illustrative purposes only, and are not intended to limit the scope of the present invention in any way. Efforts have been made to ensure accuracy with respect to numbers used (e.g., amounts, temperatures, etc.), but some experimental error and deviation should, of course, be allowed for.

The practice of the present invention will employ, unless otherwise indicated, conventional methods of molecular biology, cell biology, biochemistry, genetics, cancer biology, and pharmacology, within the skill of the art. Such techniques are explained fully in the literature.

6.6.1. Example 1: Efficacy of Lasofoxifene on ESR1 LBD Mutations

6.6.1.1. Methods

6.6.1.1.1. Site-Directed Mutagenesis

ExSite mutagenesis was performed using the corresponding primers as summarized in Table 1 below on a pENTR2B ERα WT construct using Pfu ultra taq polymerase. The primers were PNK phosphorylated. Following PCR amplification, the products were digested with DpnI at 37° C. for 1 hr, followed by overnight ligation at 16° C. Ligated products were transformed into DH5α bacterial cells and grown on kanamycin resistant plates. The pENTR clones were verified by sequencing and then swapped into the pcDNA-DEST vector using the Gateway system (Invitrogen) for expression analysis.

TABLE 1

Primers for Mutagenesis

| | | |
|---|---|---|
| ER Y537N For | AATGACCTGCTGCTGGAGATG | SEQ ID NO: 1 |
| ER Y537N Rev | GAGGGGCACCACGTTCTTGCA | SEQ ID NO: 2 |
| ER Y537S For | GACCTGCTGCTGGAGATGCTG | SEQ ID NO: 3 |
| ER Y537S Rev | GCTGAGGGGCACCACGTTCTT | SEQ ID NO: 4 |
| ER Y537C For | TGTGACCTGCTGCTGGAGATG | SEQ ID NO: 5 |
| ER Y537C Rev | GCTGAGGGGCACCACGTTCTT | SEQ ID NO: 6 |
| ER D538G For | GGTCTGCTGCTGGAGATGCTG | SEQ ID NO: 7 |
| ER D538G Rev | ATAGAGGGGCACCACGTTCTT | SEQ ID NO: 8 |

6.6.1.1.2. Cell Culture

Caov2 ovarian carcinoma cells were grown in RPMI-1640 media (Gibco) supplemented with 8% Fetal Bovine Serum (FBS), Sodium Pyruvate (NaPyr) and non-essential amino acids (NEAA) and passaged every 2-3 days. SKBR3 breast adenocarcinoma cells were grown in DMEM media (Gibco) supplemented with 8% Fetal Bovine Serum (FBS), Sodium Pyruvate (NaPyr) and non-essential amino acids (NEAA) and passaged every 2-3 days. Cells were switched into a phenol-red free RPMI-1640 media supplemented with 8% charcoal stripped fetal bovine serum (CFS), NaPyr, and NEAA one day before plating for experiment. Cells were then plated in 96-well plates for experiment in the phenol red-free media an additional day before transfection.

6.6.1.1.3. Reporter Gene Assay

Caov2 cells were co-transfected with the 7X-TK-ERE-TATA luciferase reporter gene (Nagel et al., *Endocrinology* 142(11): 4721-4728 (2001)) and expression constructs for either wild-type or mutant receptors using Fugene transfection reagent (Promega). SKBR3 cells were co-transfected with 3X-TK-ERE-TATA luciferase reporter gene in the same conditions. pCMV-β-gal was used as a control for transfection efficiency and pcDNA was added for a final DNA concentration of 75 ng per triplicate group. Cells were treated with indicated ligand five hours post transfection.

Following 24 hours of treatment, cells were lysed and the luciferase and β-gal assays were performed as described previously (Norris et al., *J Biol Chem* 270(39): 22777-22782 (1995)) and the plates were read on the Fusion α-FP HT plate reader (PerkinElmer Life Sciences).

6.6.1.2. Results

Figure 2A:
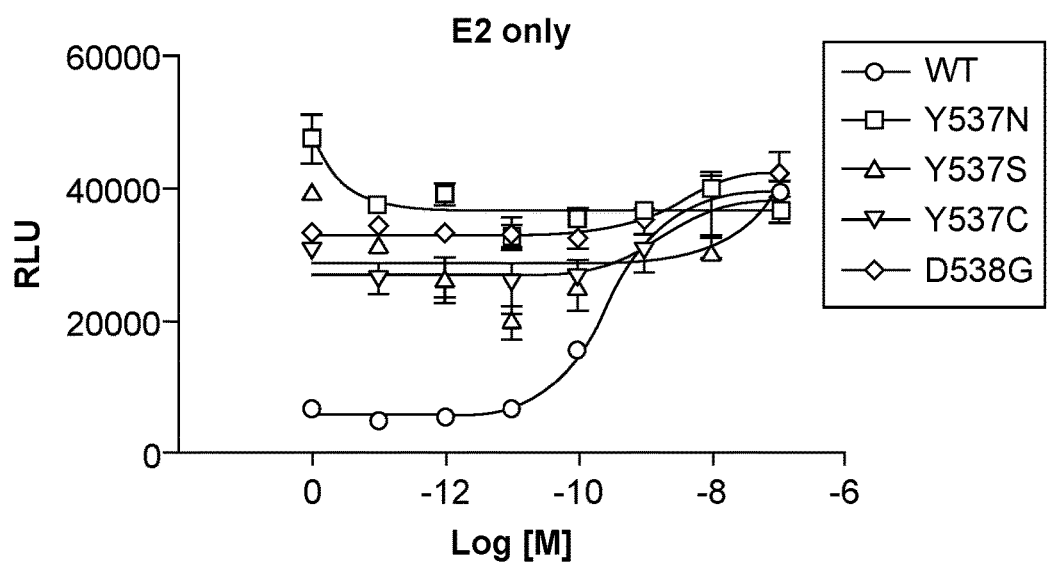
FIG. 2A and FIG. 2B show the effects of lasofoxifene on ESR1 LBD mutations in SKBR3 breast adenocarcinoma cells, with FIG. 2A demonstrating that the mutant receptors are constitutively active and do not respond to 17-β estradiol (E2), and FIG. 2B demonstrating that lasofoxifene inhibits the mutant receptor activity in a dose-response manner.

ERα expression constructs were engineered to express one of four different ESR1 LBD mutations, Y537S, Y537N, Y537C, and D538G, which are found in metastatic breast cancer patients. See Jeselsohn et al., *Nature Reviews Clinical Oncology* 12(10): 573-583 (2015); Jeselsohn et al., *Clinical Cancer Research* 20(7): 1757-1767 (2014); Robinson et al., *Nature Genetics* 45(12): 1446-1451 (2013); Thomas and Gustafsson, *Trends in Endocrinology and Metabolism* 26(9): 467-476 (2015); and Toy et al., *Nature Genetics* 45(12): 1439-1445 (2013). The activity of these mutants was evaluated in a reconstituted estrogen response element (ERE)-luciferase reporter assay in Caov2 ovarian carcinoma cells and SKBR3 breast adenocarcinoma cells. Data normalization is done in respect to the "0" data point (no ligand) of the wild-type receptor. As previously reported (Jeselsohn et al., 2014; Robinson et al., 2013; Toy et al., 2013), all of the mutants studied exhibited substantial constitutive activity when compared to the activity of wild-type (WT) ERα in the absence of its ligand: 17-β estradiol (E2). While the WT ERα responds to E2 in a dose-response matter, the transcriptional activity of the mutants is not responsive to E2 activation (FIG. 1A and FIG. 2A).

Figure 1B:
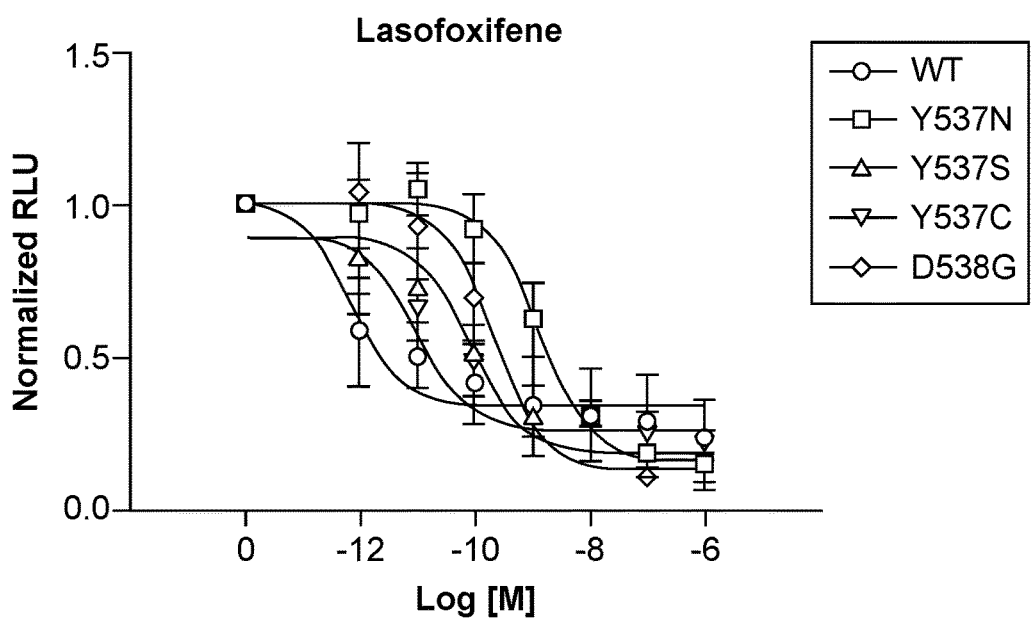
Figure 2B:
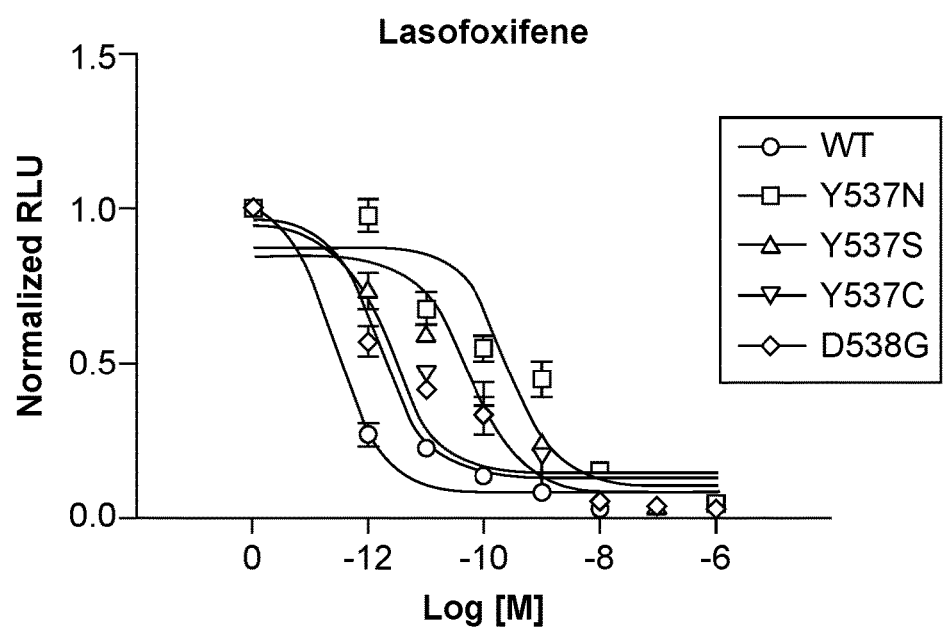

The ability of lasofoxifene to inhibit the transcriptional activity of the ERα mutants was next evaluated under the same conditions. All inhibition curves were done in the presence of $10^{-9}$ (1 nM) 17-β estradiol. Data normalization was done in respect to the "0" data point (no lasofoxifene) for each individual receptor. The plots include data from five independent experiments and each value is an average of triplicates from each experiment. Notably, lasofoxifene effectively inhibited the transcriptional activity of all tested ERα LBD mutants in a dose-response manner (FIG. 1B and FIG. 2B).

The transcriptional IC90 value of lasofoxifene was also evaluated under the same conditions in Caov2 ovarian carcinoma cells and SKBR3 breast adenocarcinoma cells. See Maximov et al., *Current Clinical Pharmacology* 8(2): 135-155 (2013). The transcriptional IC90 value of lasofoxifene evaluated was compared to the Cmax of these compounds in blood at doses used in prior clinical trials and approved in Europe. See Assessment Report for Fablyn, 2009 (EMA). The calculation included Cmax of lasofoxifene at theoretical doses of 0.5 mg and 1 mg. The additional dose of lasofoxifene (1 mg) was included to evaluate the potential clinical efficacy of lasofoxifene at a higher concentration. See Gardner et al., *J Clin Pharmacol* 46(1): 52-58 (2006). The results from Caov2 ovarian carcinoma cells and SKBR3 breast adenocarcinoma cells are summarized in Table 2.

TABLE 2

Comparison of IC90 Values to Reported Cmax Values

| Compound | Reported Cmax | Converted (M) Cmax | Caov2 IC90 | Caov2 Ratio Cmax/IC90 | SKBR3 IC90 | SKBR3 Ratio Cmax/IC90 |
|---|---|---|---|---|---|---|
| WT | | | | | | |
| Lasofoxifene (0.5 mg) | 3.6 ng/mL | 9.00E−09 | 6.68E−12 | 1346.8 | 3.30E−09 | 2.73 |
| Lasofoxifene (1 mg) | 6.43 ng/mL | 1.55E−08 | 6.68E−12 | 2320.4 | 3.30E−09 | 4.69 |
| Y537N | | | | | | |
| Lasofoxifene (0.5 mg) | 3.6 ng/mL | 9.00E−09 | 7.45E−10 | 12.08 | 1.30E−08 | 0.69 |
| Lasofoxifene (1 mg) | 6.43 ng/mL | 1.55E−08 | 7.45E−10 | 20.8 | 1.30E−08 | 1.19 |
| Y537S | | | | | | |
| Lasofoxifene (0.5 mg) | 3.6 ng/mL | 9.00E−09 | 1.22E−08 | 0.74 | 8.00E−09 | 1.13 |
| Lasofoxifene (1 mg) | 6.43 ng/mL | 1.55E−08 | 1.22E−08 | 1.27 | 8.00E−09 | 1.94 |
| Y537C | | | | | | |
| Lasofoxifene (0.5 mg) | 3.6 ng/mL | 9.00E−09 | 2.04E−10 | 44.07 | 5.90E−09 | 1.53 |
| Lasofoxifene (1 mg) | 6.43 ng/mL | 1.55E−08 | 2.04E−10 | 75.98 | 5.90E−09 | 2.63 |
| D538G | | | | | | |
| Lasofoxifene (0.5 mg) | 3.6 ng/mL | 9.00E−09 | 1.88E−09 | 4.80 | 7.10E−09 | 1.27 |
| Lasofoxifene (1 mg) | 6.43 ng/mL | 1.55E−08 | 1.88E−09 | 8.24 | 7.10E−09 | 2.18 |

As expected, the WT receptor was the most responsive to anti-estrogen treatment, with each of the mutants exhibiting reduced response to the inhibitory actions of lasofoxifene. Importantly, the pharmacology of each of the mutants was different, which highlights the need to match patients with the most appropriate drug. The data suggest that lasofoxifene at a dose of 1 mg is most effective for patients whose tumors express the mutations in both ovarian and breast cancer settings.

6.6.2. Example 2: Efficacy of Lasofoxifene on ESR1 LBD Mutations Y537S and D538G in Stable Transfectants MCF7 estrogen receptor alpha positive (ER+) breast cancer cells were engineered to stably express doxycycline (DOX)-inducible hemagglutinin (HA)-tagged full length ER with ligand binding domain mutations Y537S and D538G. The introduction and expression of the mutants were confirmed by Sanger sequencing, RNA-sequencing, and western blot.

The dose response studies were performed in full medium conditions. Cells were treated with DOX for the induction of HA-tagged mutated ER or with vehicle as control, and plated in triplicate. Subsequently, on day 5, cell counting was performed using the Celigo instrument with Hoechst dye staining to detect nucleated live cells and propidium iodide to quantify dead cells. Treatments included vehicle and increasing doses of lasofoxifene starting from $10^{-12}$ M with 10 fold increments up to $10^{-6}$ M. The efficacy of the treatment is inversely proportional to the cell count.

Figure 3A:
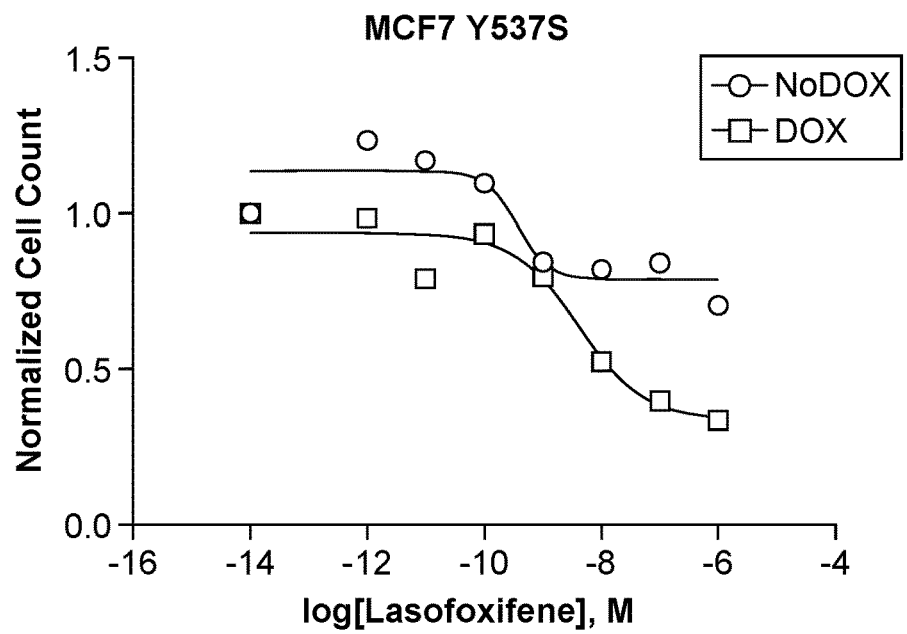
FIG. 3A and FIG. 3B show the effects of lasofoxifene on ESR1 LBD mutations in stably transfected MCF7 breast cancer cells, with FIG. 3A demonstrating that lasofoxifene inhibits the Y537S mutant receptor activity with increasing dose titration, and FIG. 3B demonstrating that lasofoxifene inhibits the D538G mutant receptor activity with increasing dose titration.
Figure 3B:
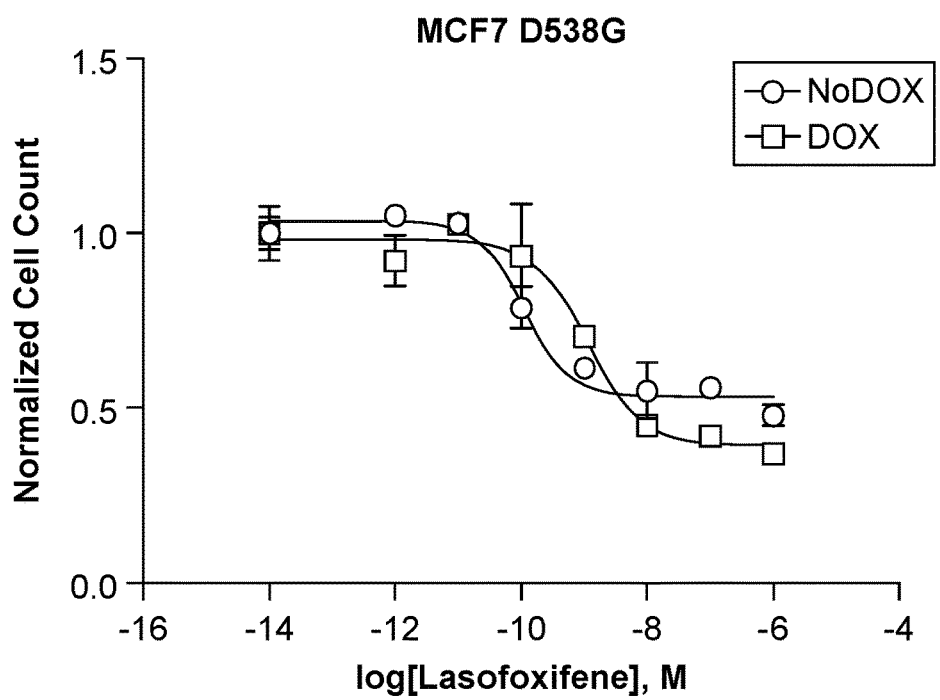

The anti-estrogenic activity of lasofoxifene in a breast cancer model of ER mutations Y537S and D538G identified in Example 1 was confirmed by the ability of lasofoxifene to overcome resistance with increasing dose titration and kill the stably transfected cells (FIG. 3A and FIG. 3B).

IC50 values were calculated using PRISM. The results are summarized in Table 3.

TABLE 3

Comparison of IC50 Values in the Absence and the Presence of DOX

| Treatment | Allele | No DOX (wt only) | DOX (ESR mutation) | Fold Change |
|---|---|---|---|---|
| Lasofoxifene | Y537S | 3.6E-10 | 4.1E-9 | 11.4 |
| Lasofoxifene | D538G | 1E-10 | 1E-9 | 10 |

The results confirmed that lasofoxifene treatment is effective on the Y537S and D538G mutations, although the Y537S and D538G mutations require higher concentrations to overcome resistance.

7. EQUIVALENTS AND INCORPORATION BY REFERENCE

While the invention has been particularly shown and described with reference to a preferred embodiment and various alternate embodiments, it will be understood by persons skilled in the relevant art that various changes in form and details can be made therein without departing from the spirit and scope of the invention.

All references, issued patents and patent applications cited within the body of the instant specification are hereby incorporated by reference in their entirety, for all purposes.

The invention claimed is:

1. A method of reducing the progression of estrogen receptor positive (ER+) locally advanced or metastatic breast cancer in a patient, wherein the cancer has at least one gain of function missense mutation within the ligand binding domain (LBD) of the Estrogen Receptor 1 (ESR1) gene, the method comprising:
   administering to the patient an effective amount of lasofoxifene or a pharmaceutically acceptable salt thereof.

2. The method of claim 1, wherein the cancer has previously been determined to have at least one gain of function missense mutation within the ligand binding domain (LBD) of the Estrogen Receptor 1 (ESR1) gene.

3. The method of claim 1, further comprising the earlier step of: determining that the cancer has at least one gain of function missense mutation within the ligand binding domain (LBD) of the Estrogen Receptor 1 (ESR1) gene.

4. The method of claim 1, wherein the at least one of gain of function missense mutation is in any one of amino acids D538, Y537, L536, P535, V534, 5463, V392, and E380 of the ERα protein.

5. The method of claim 4, wherein the at least one of gain of function missense mutation is D538G, Y537S, Y537N, Y537C, Y537Q, L536R, L536Q, P535H, V534E, S463P, V392I, or E380Q.

6. The method of claim 4, wherein the at least one of gain of function missense mutation is in amino acid D538 or Y537 of the ERα protein.

7. The method of claim 6, wherein the at least one of gain of function missense mutation is D538G, Y537S, Y537N, Y537C, or Y537Q.

8. The method of claim 1, wherein the patient has previously been treated with one or more lines of endocrine therapy.

9. The method of claim 8, wherein the endocrine therapy that the patient has previously been treated with is a selective ER modulator (SERM), a selective ER degrader (SERD), or an aromatase inhibitor (AI).

10. The method of claim 9, wherein the endocrine therapy that the patient has previously been treated with is an aromatase inhibitor.

11. The method of claim 10, wherein the aromatase inhibitor is exemestane, letrozole, or anastrozole.

12. The method of claim 8, wherein the patient has had disease progression after endocrine therapy.

13. The method of claim 1, wherein the patient is post-menopausal.

14. The method of claim 1, wherein lasofoxifene is administered as lasofoxifene tartrate.

15. The method of claim 1, wherein lasofoxifene is administered by oral administration.

16. The method of claim 15, wherein lasofoxifene is administered at 5 mg/day per OS.

17. The method of claim 1, further comprising administering to the patient an effective amount of cyclin-dependent kinase 4/6 (CDK4/6) inhibitor.

* * * * *

SEQUENCE LISTING

```
<160> NUMBER OF SEQ ID NOS: 8

<210> SEQ ID NO 1
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
aatgacctgc tgctggagat g                                           21

<210> SEQ ID NO 2
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
gaggggcacc acgttcttgc a                                           21

<210> SEQ ID NO 3
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
gacctgctgc tggagatgct g                                           21

<210> SEQ ID NO 4
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
```

```
gctgaggggc accacgttct t                                              21

<210> SEQ ID NO 5
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
tgtgacctgc tgctggagat g                                              21

<210> SEQ ID NO 6
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
gctgaggggc accacgttct t                                              21

<210> SEQ ID NO 7
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
ggtctgctgc tggagatgct g                                              21

<210> SEQ ID NO 8
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
atagaggggc accacgttct t                                              21
```